United States Patent
Dogra et al.

(10) Patent No.: US 10,544,123 B2
(45) Date of Patent: Jan. 28, 2020

(54) BLUE LUMINESCENT COMPOUNDS

(71) Applicant: LG Chem, Ltd., Seoul (KR)

(72) Inventors: Kalindi Dogra, Wilmington, DE (US); Juergen Weber, Lincoln University, PA (US)

(73) Assignee: LG Chem, Ltd. (KR)

( * ) Notice: Subject to any disclaimer, the term of this patent is extended or adjusted under 35 U.S.C. 154(b) by 265 days.

(21) Appl. No.: 15/518,262

(22) PCT Filed: Oct. 16, 2015

(86) PCT No.: PCT/US2015/055927
§ 371 (c)(1),
(2) Date: Apr. 11, 2017

(87) PCT Pub. No.: WO2016/064671
PCT Pub. Date: Apr. 28, 2016

(65) Prior Publication Data
US 2018/0282299 A1    Oct. 4, 2018

Related U.S. Application Data

(60) Provisional application No. 62/065,815, filed on Oct. 20, 2014.

(51) Int. Cl.
*H01L 51/50* (2006.01)
*C07D 401/10* (2006.01)
(Continued)

(52) U.S. Cl.
CPC ......... *C07D 401/10* (2013.01); *C07D 209/86* (2013.01); *C07D 401/14* (2013.01);
(Continued)

(58) Field of Classification Search
None
See application file for complete search history.

(56) References Cited

U.S. PATENT DOCUMENTS 7,351,358 B2   4/2008 Hsu et al.
2004/0102577 A1  5/2004 Hsu et al.
(Continued)

FOREIGN PATENT DOCUMENTS

CN    103187531 A    7/2013
CN    103189469 A    7/2013
(Continued)

OTHER PUBLICATIONS

Written_Opinion_InternationalApplicationNo. PCTUS2015055927_ISA_KR_AuthorizedOffice_Han_Sol_Cho_dated Sep. 2, 2016.
(Continued)

*Primary Examiner* — Gregory D Clark
(74) *Attorney, Agent, or Firm* — Lerner, David, Littenberg, Krumholz & Mentlik, LLP

(57) ABSTRACT

There is provided a compound having Formula I, Formula II, Formula III, Formula IV, Formula V, or Formula VI:
(Continued)

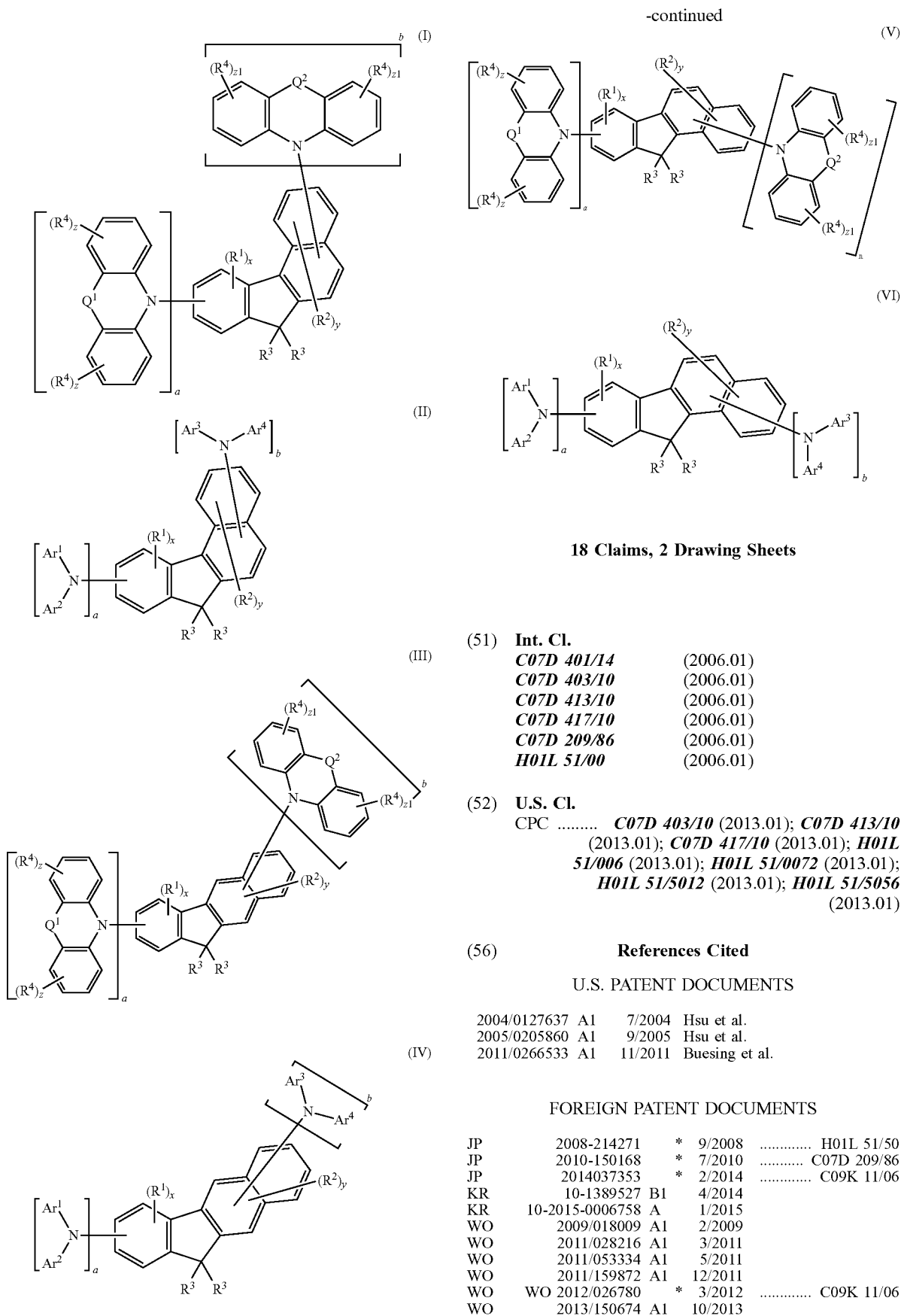

(56) References Cited

FOREIGN PATENT DOCUMENTS

WO 2014/065391 A1 5/2014
WO 2015/089304 A1 6/2015

OTHER PUBLICATIONS

Wang_Y_Kirk_Othmer_Encyclopedia_of_Chemical_Technology_Fourth_Edition_vol. 18_837 860_1996.

International_Search_Report_International_Application_No. PCTUS2015055927_ISA_KR_AuthorizedOfficer_Han_So_Cho_dated Sep. 2, 2016.
Gustafsson_FlexibleLightEmittingDiodes_Nature_Jun. 11, 1992_vol. 357_pp. 477-479.
CRC Handbook of Chemistry and Physics, 81st Edition (2000-2001)_Book_Not_Included.
Chinese Search Report for Application No. 201580055201.4, dated Aug. 5, 2019, pp. 1-2.

* cited by examiner

BLUE LUMINESCENT COMPOUNDS

RELATED APPLICATION DATA

The present application is a national phase entry under 35 U.S.C. § 371 of International Application No. PCT/US2015/055927, filed on Oct. 16, 2015, which claims priority under 35 U.S.C. § 119(e) from U.S. Provisional Application No. 62/065,815, filed on Oct. 20, 2014, the disclosures of which are incorporated by reference herein.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I, as described below in the detailed description.

There is also provided a compound having Formula I-a, as described below in the detailed description.

There is also provided a compound having Formula II, as described below in the detailed description.

There is also provided a compound having Formula II-a, as described below in the detailed description.

There is also provided a compound having Formula III, as described below in the detailed description.

There is also provided a compound having Formula III-a, as described below in the detailed description.

There is also provided a compound having Formula IV, as described below in the detailed description.

There is also provided a compound having Formula IV-a, as described below in the detailed description.

There is also provided a compound having Formula V, as described below in the detailed description.

There is also provided a compound having Formula V-a, as described below in the detailed description.

There is also provided a compound having Formula V-b, as described below in the detailed description.

There is also provided a compound having Formula VI, as described below in the detailed description.

There is also provided a compound having Formula VI-a, as described below in the detailed description.

There is also provided a compound having Formula VI-b, as described below in the detailed description.

There is also provided an organic electronic device comprising a first electrical contact, a second electrical contact and a photoactive layer therebetween, the photoactive layer comprising a compound having Formula I, Formula I-a, Formula II, Formula II-a, Formula III, Formula III-a, Formula IV, Formula IV-a, Formula V, Formula V-a, Formula V-b, Formula VI, Formula VI-a, or Formula VI-b.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
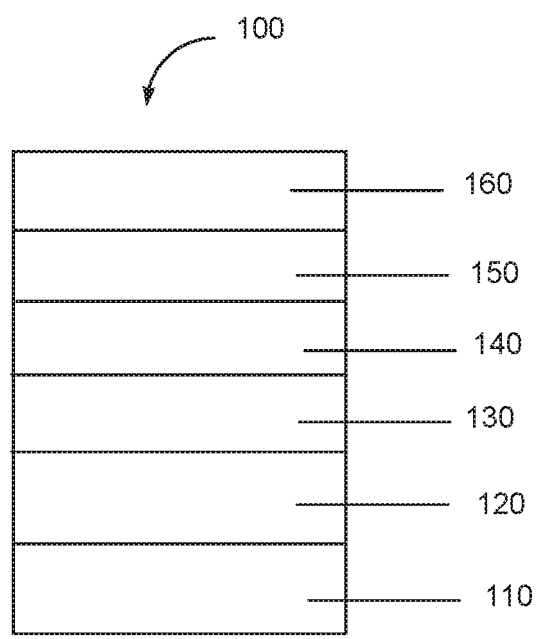
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compounds, Compounds Having Formula I or Formula I-a, Compounds Having Formula II or Formula II-a, Compounds Having Formula III or Formula III-a, Compounds Having Formula IV or Formula IV-a, Compounds Having Formula V, Formula V-a, or Formula V-b, Compounds Having Formula VI, Formula VI-a, or Formula VI-b, Devices, and finally Examples.

1. Definitions and Clarification of Terms

Before addressing details of embodiments described below, some terms are defined or clarified.

The term "adjacent" as it refers to substituent groups refers to groups that are bonded to carbons that are joined together with a single or multiple bond. Exemplary adjacent R groups are shown below:

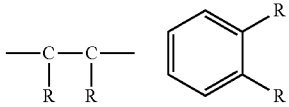

The term "alkoxy" is intended to mean the group RO—, where R is an alkyl group.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having 4n+2 delocalized pi electrons.

The term "aryl" is intended to mean a group derived from an aromatic hydrocarbon having one point of attachment. The term includes groups which have a single ring and those which have multiple rings which can be joined by a single bond or fused together. Hydrocarbon aryl groups have only carbon in the ring structures. Heteroaryl groups have at least one heteroatom in a ring structure. The term "alkylaryl" is intended to mean an aryl group having one or more alkyl substituents.

The term "aryloxy" is intended to mean the group RO—, where R is an aryl group.

The term "benzofluorene" includes three isomers as shown below.

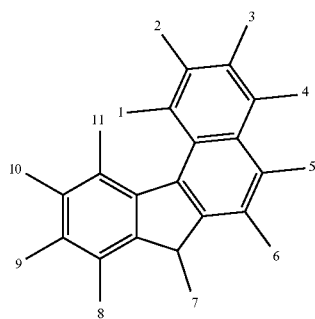

BzF-1

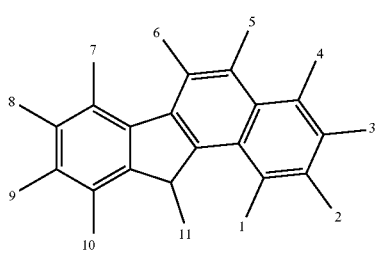

BzF-2

BzF-3 where the numbers indicate the position on the core. It will be understood that there can be two groups at position 7 in BzF-1 and two groups at position 11 in BzF-2 and BzF-3.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group R₃SiO—, where R is the same or different at each occurrence and is H, D, C1-20 alkyl, deuterated alkyl, fluoroalkyl, aryl, or deuterated aryl.

The term "silyl" refers to the group R₃Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

All groups may be unsubstituted or substituted. The substituent groups are discussed below. In a structure where a substituent bond passes through one or more rings as shown below,

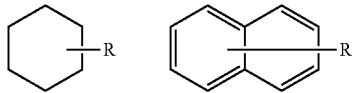

it is meant that the substituent R may be bonded at any available position on the one or more rings.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds

In some embodiments, the new compounds described herein are useful as emissive materials. In some embodiments, the new compounds are blue emissive materials. They can be used alone or as a dopant in a host material.

In some embodiments, the new compounds described herein have deep blue color. As used herein, the term "deep blue color" refers to a c.i.e. y-coordinate of less than 0.10, according to the C.I.E. chromaticity scale (Commission Internationale de L'Eclairage, 1931). In some embodiments, the new compounds described herein have a photoluminescence y-coordinate of less than 0.10; in some embodiments, less than 0.090.

In some embodiments, devices including the new compounds described herein have improved efficiencies. In some embodiments, the efficiency of devices including the new compounds described herein is greater than 4.5 cd/A at 1000 nits; in some embodiments, greater than 5.0 cd/A at 1000 nits.

In some embodiments, devices including the new compounds described herein have increased lifetime. In some embodiments, devices including the new compounds described herein have a T70 greater than 1000 hours at 50° C. As used herein, T70 refers to the time to reach 70% of initial luminance. In some embodiments, devices including the new compounds described herein have a T70 greater than 1500 hours at 50° C.

In some embodiments, electroluminescent devices including the new compounds described herein as emissive materials have deep blue color. In some embodiments, the x-coordinate is less than 0.15 and the y-coordinate is less than 0.10; in some embodiments, the y-coordinate is less than 0.090.

In some embodiments of the new compounds described herein, the new compound is deuterated. In some embodiments, the new compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of the new compounds described herein, deuteration is present on the core benzofluorene group.

In some embodiments of the new compounds described herein, deuteration is present on one or more substituent groups.

In some embodiments of the new compounds described herein, deuteration is present on the core benzofluorene group and one or more substituent groups.

The new compounds described herein can be made using any technique that will yield a C—C or C—N bond. A variety of such techniques are known, such as Suzuki, Yamamoto, Stille, and metal-catalyzed C—N couplings as well as metal catalyzed and oxidative direct arylation.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, trifluoromethanesulfonic acid, etc. Deuteration reactions have also been described in published PCT application WO2011/053334.

Exemplary preparations are given in the Examples.

3. Compounds Having Formula I or Formula I-a

The compounds of Formula I and Formula I-a have a benzofluorene core with two amino groups directly attached, wherein each amino nitrogen has two aryl groups attached.

The compounds having Formula I or Formula I-a have the core benzofluorene structure BzF-1, as described above.

In some embodiments, the compounds have Formula I:

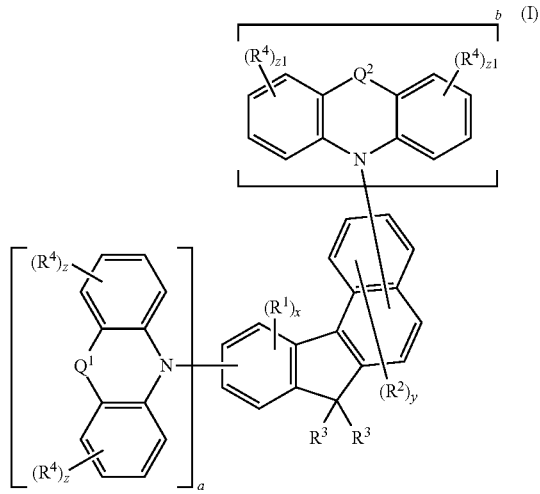

wherein:
- $Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;
- $R^1$, $R^2$ and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;
- $R^5$ is the same or different at each occurrence and is selected from the group consisting of H, D, F, alkyl, fluoroalkyl, deuterated alkyl, or deuterated partially-fluorinated alkyl;
- $R^6$ is selected from the group consisting of aryl and deuterated aryl;
- a and b are the same or different and are 0 or 1, with the proviso that a+b≥1;
- w is an integer of 1-6;
- x is an integer of 0-4, with the proviso that when a=1, x=0-3;
- y is an integer of 0-6, with the proviso that when b=1, y=0-5;
- z is an integer of 0-5, with the proviso that when $Q^1$ is not nil, z is 0-4; and
- z1 is an integer of 0-5, with the proviso that when $Q^2$ is not nil, z1 is 0-4.

In some embodiments of Formula I, $Q^1$ is nil. By "nil" it is meant that there is no bond connecting the two aryl groups on the nitrogen. The "two aryl groups on the nitrogen" do not include the benzofluorene core.

In some embodiments of Formula I, $Q^2$ is nil.

In some embodiments of Formula I, both $Q^1$ and $Q^2$ are present and are not nil.

In some embodiments of Formula I, a=1, b=0, and $Q^1$ is not nil.

In some embodiments of Formula I, a=0, b=1, and $Q^2$ is not nil.

In some embodiments of Formula I, a=b=1.

In some embodiments of Formula I, a=1 and the amino nitrogen is bonded to position 8 on the benzofluorene core.

In some embodiments of Formula I, a=1 and the amino nitrogen is bonded to position 9 on the benzofluorene core.

In some embodiments of Formula I, a=1 and the amino nitrogen is bonded to position 10 on the benzofluorene core.

In some embodiments of Formula I, a=1 and the amino nitrogen is bonded to position 11 on the benzofluorene core.

In some embodiments of Formula I, b=1 and the amino nitrogen is bonded to position 1 on the benzofluorene core.

In some embodiments of Formula I, b=1 and the amino nitrogen is bonded to position 2 on the benzofluorene core.

In some embodiments of Formula I, b=1 and the amino nitrogen is bonded to position 3 on the benzofluorene core.

In some embodiments of Formula I, b=1 and the amino nitrogen is bonded to position 4 on the benzofluorene core.

In some embodiments of Formula I, b=1 and the amino nitrogen is bonded to position 6 on the benzofluorene core.

In some embodiments of Formula I, $Q^1$ is a single bond. By this it is meant that the two aryl groups on the nitrogen are connected by a single bond. The "two aryl groups on the nitrogen" do not include the benzofluorene core.

In some embodiments of Formula I, $Q^1=(CR^5{}_2)_w$.

In some embodiments of Formula I, $R^5$ is H or D.

In some embodiments of Formula I, $R^5$ is an alkyl or deuterated alkyl of 1-20 carbons; in some embodiments, 1-10 carbons; in some embodiments, 1-3 carbons.

In some embodiments of Formula I, $R^5$ is a fluoroalkyl or deuterated partially-fluorinated alkyl of 1-20 carbons; in some embodiments, 1-10 carbons; in some embodiments, 1-3 carbons.

In some embodiments of Formula I, one $R^5$ is H or D and one $R^5$ is alkyl or deuterated alkyl.

In some embodiments of Formula I, one $R^5$ is H or D and one $R^5$ is fluorinated alkyl or deuterated partially-fluorinated alkyl.

In some embodiments of Formula I, $R^5$ is alkyl or deuterated alkyl, and the two $R^5$ groups are joined together to form a 5- or 6-membered ring.

In some embodiments of Formula I, w is 1.
In some embodiments of Formula I, w is 2.
In some embodiments of Formula I, w is 3.
In some embodiments of Formula I, w is 4.
In some embodiments of Formula I, w is 5.
In some embodiments of Formula I, w is 6.
In some embodiments of Formula I, $Q^1=NR^6$.
In some embodiments of Formula I, $R^6$ is selected from the group consisting of phenyl, biphenyl, naphthyl, and deuterated analogs thereof.

In some embodiments of Formula I, $Q^1$=O.
In some embodiments of Formula I, $Q^1$=S.
In some embodiments of Formula I, $Q^1$=Se.
In some embodiments of Formula I, $Q^2$ is a single bond.
In some embodiments of Formula I, $Q^2$=$(CR^5{}_2)_w$.
In some embodiments of Formula I, $Q^2$=$NR^6$.
In some embodiments of Formula I, $Q^2$=O.
In some embodiments of Formula I, $Q^2$=S.
In some embodiments of Formula I, $Q^2$=Se.
In some embodiments of Formula I, at least one of $Q^1$ and $Q^2$ is a single bond.
In some embodiments of Formula I, at least one of $Q^1$ and $Q^2$ is $(CR^5{}_2)_w$.
In some embodiments of Formula I, x=0.
In some embodiments of Formula I, x=1.
In some embodiments of Formula I, x=2.
In some embodiments of Formula I, x=3.
In some embodiments of Formula I, x=4.
In some embodiments of Formula I, x>0.
In some embodiments of Formula I, x>0 and at least one $R^1$ is D.
In some embodiments of Formula I, x>0 and at least one of $R^1$ is alkyl or deuterated alkyl.
In some embodiments, the alkyl or deuterated alkyl has 1-12 carbons; in some embodiments, 3-8 carbons; in some embodiments, 1-4 carbons.
In some embodiments of Formula I, y=0.
In some embodiments of Formula I, y=1.
In some embodiments of Formula I, y=2.
In some embodiments of Formula I, y=3.
In some embodiments of Formula I, y=4.
In some embodiments of Formula I, y>0.
In some embodiments of Formula I, y>0 and at least one $R^2$ is D.
In some embodiments of Formula I, y>0 and at least one of $R^2$ is alkyl or deuterated alkyl.
In some embodiments of Formula I, $R^3$ is selected from the group consisting of alkyl and deuterated alkyl having 1-12 carbons; in some embodiments, 3-8 carbons; in some embodiments 1-4 carbons.
In some embodiments of Formula I, the two $R^3$ groups are joined together to form a 5- or 6-membered aliphatic ring.
In some embodiments of Formula I, $R^3$ is selected from the group consisting of aryl and deuterated aryl.
In some embodiments of Formula I, $R^3$ is selected from the group consisting of phenyl and deuterated phenyl.
In some embodiments of Formula I, the two $R^3$ groups are phenyl groups which are joined together to form a spirofluorene group.
In some embodiments of Formula I, z=0.
In some embodiments of Formula I, at least one z>0.
In some embodiments of Formula I, at least one z=1.
In some embodiments of Formula I, at least one z=2.
In some embodiments of Formula I, at least one z=3.
In some embodiments of Formula I, at least one z=4.
In some embodiments of Formula I, at least one z=5.
In some embodiments of Formula I, z1=0.
In some embodiments of Formula I, at least one z1>0.
In some embodiments of Formula I, at least one z1=1.
In some embodiments of Formula I, at least one z1=2.
In some embodiments of Formula I, at least one z1=3.
In some embodiments of Formula I, at least one z1=4.
In some embodiments of Formula I, at least one z1=5.
In some embodiments of Formula I, at least one $R^4$ is present and is selected from the group consisting of aryl, heteroaryl, and deuterated analogs thereof.

In some embodiments of Formula I, at least one $R^4$ group is present and is selected from the group consisting of heteroaryl and deuterated heteroaryl, where the heteroaryl has at least one ring atom which is selected from the group consisting of N, O, and S.

In some embodiments of Formula I, at least one $R^4$ is present and is an N-heteroaryl or deuterated N-heteroaryl having at least one ring atom which is N.

In some embodiments, the N-heteroaryl is selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, indole, indoloindole, substituted derivatives thereof, and deuterated analogs thereof.

In some embodiments, the N-heteroaryl is a carbazole or deuterated carbazole.

In some embodiments, the N-heteroaryl is a carbazole or deuterated carbazole having formula Cz-1:

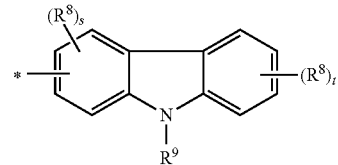

wherein:
$R^8$ is the same or different at each occurrence and is selected from the group consisting of D, alkyl, silyl, aryl, deuterated alkyl, deuterated silyl, and deuterated aryl;
$R^9$ is selected from the group consisting of aryl and deuterated aryl;
s is an integer of 0-3;
t is an integer of 0-4; and
represents the point of attachment.

In some embodiments, the N-heteroaryl is a carbazole or deuterated carbazole having formula Cz-2:

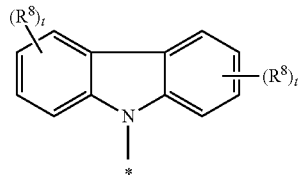

where $R^8$, $R^9$, t, and * are as defined above for Cz-1.

In some embodiments, the N-heteroaryl is a carbazole or deuterated carbazole having formula Cz-3:

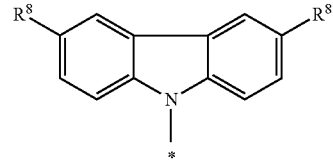

where $R^8$ and * are as defined above for Cz-1.

In some embodiments, the N-heteroaryl is a carbazole or deuterated carbazole having formula Cz-4:

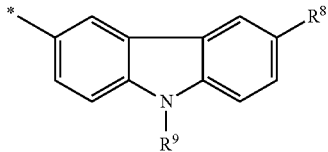

Cz-4 where $R^8$, $R^9$ and * are as defined above for Cz-1.

In some embodiments, the N-heteroaryl is a carbazole or deuterated carbazole having formula Cz-5:

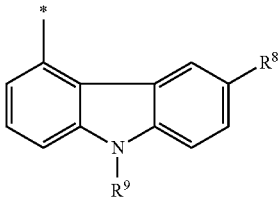

Cz-5 where $R^8$, $R^9$ and * are as defined above for Cz-1.

In some embodiments, the N-heteroaryl is a benzimidazole or deuterated benzimidazole having formula BzI-1:

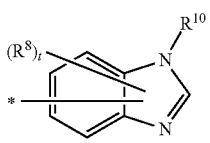

BzI-1 where $R^{10}$ is selected from the group consisting of alkyl, aryl, and deuterated analogs thereof; $R^8$ and * are as defined above for Cz-1.

In some embodiments, the N-heteroaryl is a benzimidazole or deuterated benzimidazole having formula BzI-2:

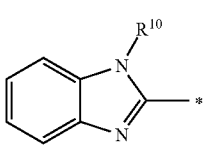

BzI-2 where $R^{19}$ and * are as defined above for BzI-1.

In some embodiments of Formula I, at least one $R^4$ is present and is an S-heteroaryl having at least one ring atom which is S.

In some embodiments, the S-heteroaryl is selected form the group consisting of thiophene, benzothiophene, dibenzothiophene, and deuterated analogs thereof.

In some embodiments, the S-heteroaryl is a dibenzothiophene or deuterated dibenzothiophene.

In some embodiments, the S-heteroaryl is a dibenzothiophene or deuterated dibenzothiophene having formula DBT-1

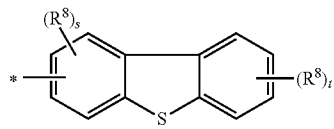

DBT-1 where $R^8$, $R^9$ and * are as defined above for Cz-1.

In some embodiments, the S-heteroaryl is a dibenzothiophene or deuterated dibenzothiophene having formula DBT-2:

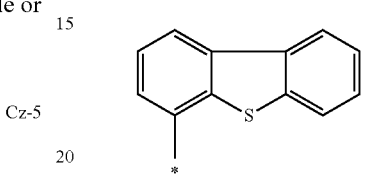

DBT-2 where * represents the point of attachment.

In some embodiments, the S-heteroaryl is a dibenzothiophene or deuterated dibenzothiophene having formula DBT-3:

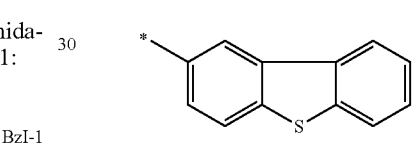

DBT-3 wherein * represents the point of attachment.

In some embodiments of Formula I, at least one $R^4$ is present and is an O-heteroaryl having at least one ring atom that is O.

In some embodiments, the O-heteroaryl is selected from the group consisting of furan, benzofuran, dibenzofuran, and deuterated analogs thereof.

In some embodiments, the O-heteroaryl is a dibenzofuran or deuterated dibenzofuran.

In some embodiments, the O-heteroaryl is a dibenzofuran or deuterated dibenzofuran having formula DBF-1:

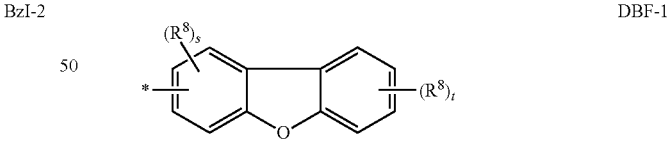

DBF-1 where $R^8$, $R^9$ and * are as defined above for Cz-1.

In some embodiments, the O-heteroaryl is a dibenzofuran or deuterated dibenzofuran having formula DBF-2:

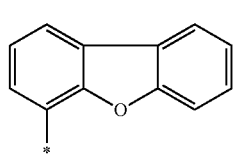

DBF-2 where * represents the point of attachment.

In some embodiments, the O-heteroaryl is a dibenzofuran or deuterated dibenzofuran having formula DBF-3:

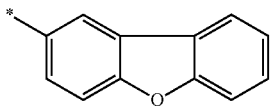

DBF-3 where * represents the point of attachment.

In some embodiments of Formula I, at least one $R^4$ is present and is an N,O-heteroaryl having at least one ring atom that is N and at least one ring atom that is O.

In some embodiments, the N,O-heteroaryl is selected from the group consisting of oxazole, benzoxazole, and deuterated analogs thereof.

In some embodiments, the N,O-heteroaryl is a benzoxazole or deuterated benzoxazole having formula BzO-1:

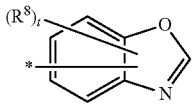

BzO-1 where $R^8$ and * are as defined above for Cz-1.

In some embodiments, the N,O-heteroaryl is a benzoxazole or deuterated benzoxazole having formula BzO-2:

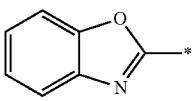

BzO-2 where * represents the point of attachment.

In some embodiments of Formula I, at least one $R^4$ is present and is an N,S-heteroaryl having at least one ring atom that is N and at least one ring atom that is S.

In some embodiments, the N,S-heteroaryl is selected from the group consisting of thiazole, benzothiazole, and deuterated analogs thereof.

In some embodiments, the N,S-heteroaryl is a benzothiazole or deuterated benzothiazole having formula BT-1:

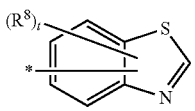

BT-1 where $R^8$ and * are as defined above for Cz-1.

In some embodiments, the N,S-heteroaryl is a benzothiazole or deuterated benzothiazole having formula BT-2:

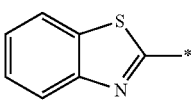

BT-2 where * represents the point of attachment.

In some embodiments of Formula I, at least one $R^4$ is present and is a hydrocarbon aryl.

In some embodiments, the hydrocarbon aryl has 6-30 ring carbons; in some embodiments, 6-20 ring carbons.

In some embodiments of Formula I, at least one $R^4$ is present and is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of D, F, CN, alkyl, fluoroalkyl, alkoxy, silyl, siloxane, siloxy, deuterated alkyl, deuterated partially-fluorinated alkyl, deuterated alkoxy, deuterated silyl, deuterated siloxane, and deuterated siloxy.

In some embodiments of Formula I, at least one $R^4$ is present and has Formula a

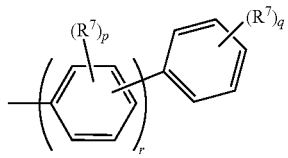

Formula a where:
$R^7$ is the same or different at each occurrence and is selected from the group consisting of D, alkyl, aryloxy, heteroaryl, alkoxy, siloxy, silyl, germyl, deuterated alkyl, deuterated aryloxy, deuterated heteroaryl, deuterated alkoxy, deuterated siloxane, deuterated silyl, deuterated germyl, where adjacent $R^7$ groups can be joined together to form a fused ring;
p is the same or different at each occurrence and is an integer from 0-4;
q is an integer from 0-5; and
r is an integer from 0 to 5.

In some embodiments, at least one $R^4$ is present and has Formula b

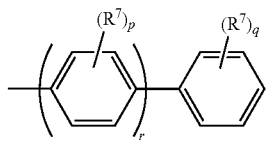

Formula b where $R^7$, p, q, and r are as in Formula a.

In some embodiments, the compounds have Formula I-a:

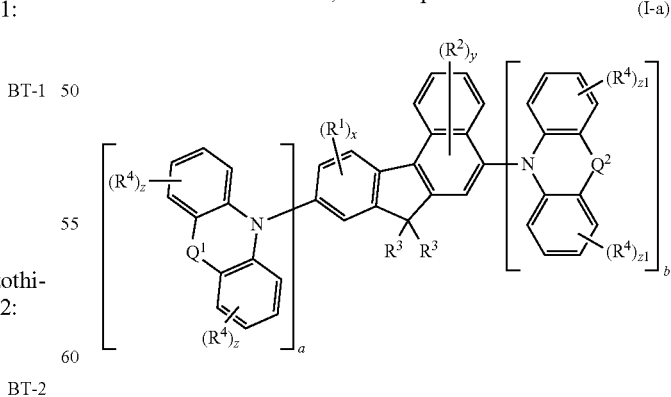

(I-a)

wherein:
$Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;

R¹, R² and R⁴ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

R³ is the same or different at each occurrence and is selected from the group consisting of alkyl, silyl, germyl, aryl, and deuterated analogs thereof, where two alkyl R³ groups can be joined together to make a cycloalkyl spiro ring, and where two R³ phenyl groups can be joined to form a spiro fluorene group;

R⁵ is the same or different at each occurrence and is selected from the group consisting of H, D, F, alkyl, fluoroalkyl, deuterated alkyl, or deuterated partially-fluorinated alkyl;

R⁶ is selected from the group consisting of aryl and deuterated aryl;

a and b are the same or different and are 0 or 1, with the proviso that a+b≥1;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when Q¹ is not nil, z is 0-4; and z1 is an integer of 0-5, with the proviso that when Q² is not nil, z1 is 0-4.

All of the embodiments for a, b, Q¹, Q², R¹, R², R³, R⁴, w, x, y, z, and z1 as described above for Formula I apply equally to Formula I-a.

Any of the above embodiments of Formula I or Formula I-a can be combined with one or more of the other embodiments, so long as they are not mutually exclusive. For example, the embodiment in which at least one x>0 and at least one R¹ is D can be combined with the embodiment in which at least one z1>0 and R⁴ is an N,S-heteroaryl or deuterated N,S-heteroaryl. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula I include, but are not limited to, the compounds shown below.

Compound I-1 BD3501

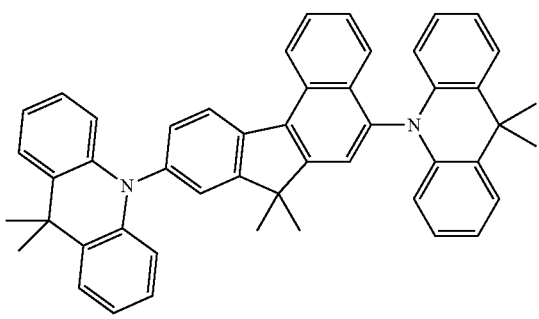

Compound I-2

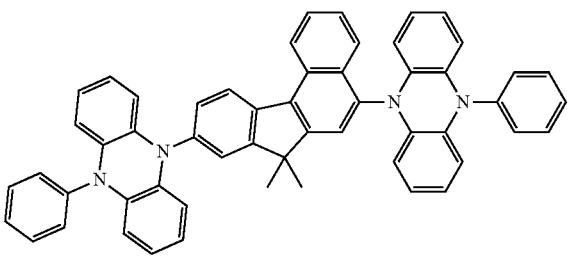

Compound I-3

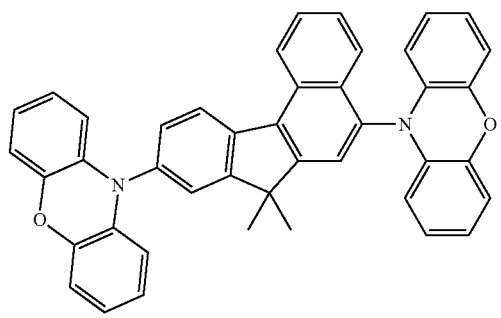

Compound I-4 (BD3839)

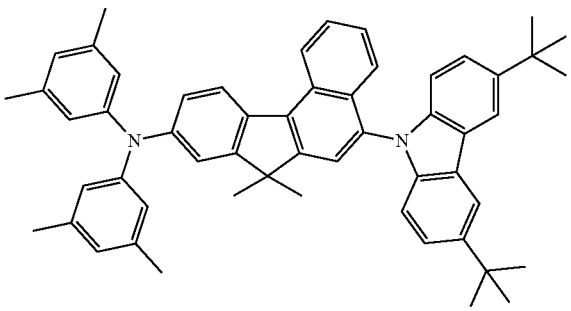

Compound I-5 (BD3847)

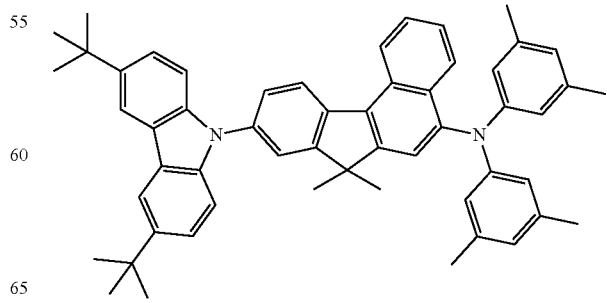

4. Compounds Having Formula II or Formula II-a

The compounds of Formula II and Formula II-a have the core benzofluorene structure BzF-1, as described above.

In some embodiments, the compounds have Formula II:

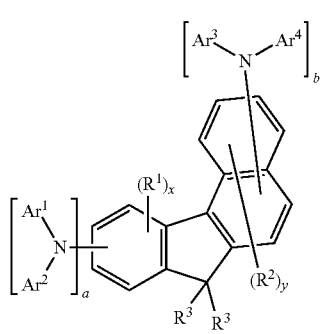

(II)

wherein:
- $Ar^1$-$Ar^4$ are the same or different and are selected from the group consisting of hydrocarbon aryl, heteroaryl, and deuterated analogs thereof, with the proviso that at least one of $Ar^1$-$Ar^4$ is heteroaryl or deuterated heteroaryl;
- $R^1$ and $R^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;
- a and b are the same or different and are 0 or 1, with the proviso that $a+b \geq 1$;
- x is an integer of 0-4, with the proviso that when a=1, x=0-3; and
- y is an integer of 0-6, with the proviso that when b=1, y=0-5. All of the embodiments of $R^1$, $R^2$, $R^3$, a, b, x and y described above for Formula I apply equally to Formula II.

In some embodiments of Formula II, a=1 and the amino nitrogen is bonded to position 8 on the benzofluorene core.

In some embodiments of Formula II, a=1 and the amino nitrogen is bonded to position 9 on the benzofluorene core.

In some embodiments of Formula II, a=1 and the amino nitrogen is bonded to position 10 on the benzofluorene core.

In some embodiments of Formula II, a=1 and the amino nitrogen is bonded to position 11 on the benzofluorene core.

In some embodiments of Formula II, b=1 and the amino nitrogen is bonded to position 1 on the benzofluorene core.

In some embodiments of Formula II, b=1 and the amino nitrogen is bonded to position 2 on the benzofluorene core.

In some embodiments of Formula II, b=1 and the amino nitrogen is bonded to position 3 on the benzofluorene core.

In some embodiments of Formula II, b=1 and the amino nitrogen is bonded to position 4 on the benzofluorene core.

In some embodiments of Formula II, b=1 and the amino nitrogen is bonded to position 6 on the benzofluorene core.

In Formula II, at least one of $Ar^1$-$Ar^4$ is heteroaryl or deuterated heteroaryl, and the heteroaryl ring is bonded directly to the amino nitrogen. When the heteroaryl group has two or more fused rings, the group is bonded directly to the amino nitrogen through any available position on any of the fused rings.

When a=0, at least one of $Ar^3$ and $Ar^4$ is heteroaryl or deuterated heteroaryl. When b=0, at least one of $Ar^1$ and $Ar^2$ is heteroaryl or deuterated heteroaryl.

In some embodiments of Formula II, two of $Ar^1$-$Ar^4$ are heteroaryl or deuterated heteroaryl.

In some embodiments of Formula II, three of $Ar^1$-$Ar^4$ are heteroaryl or deuterated heteroaryl.

In some embodiments of Formula II, all of $Ar^1$-$Ar^4$ are heteroaryl or deuterated heteroaryl.

In some embodiments of Formula II, $Ar^1$ is heteroaryl or deuterated heteroaryl.

In some embodiments of Formula II, $Ar^2$ is heteroaryl or deuterated heteroaryl.

In some embodiments of Formula II, $Ar^3$ is heteroaryl or deuterated heteroaryl.

In some embodiments of Formula II, $Ar^4$ is heteroaryl or deuterated heteroaryl.

In some embodiments of Formula II, $Ar^1=Ar^2$.
In some embodiments of Formula II, $Ar^1 \neq Ar^2$.
In some embodiments of Formula II, $Ar^1=Ar^3$.
In some embodiments of Formula II, $Ar^1 \neq Ar^3$.
In some embodiments of Formula II, $Ar^2=Ar^4$.
In some embodiments of Formula II, $Ar^2 \neq Ar^4$.
In some embodiments of Formula II, $Ar^3=Ar^4$.
In some embodiments of Formula II, $Ar^3 \neq Ar^4$.

In some embodiments of Formula II, at least one of $Ar^1$-$Ar^4$ is a heteroaryl having at least one ring atom which is selected from the group consisting of N, O, and S.

In some embodiments of Formula II, at least one of $Ar^1$-$Ar^4$ is an N-heteroaryl or deuterated N-heteroaryl having at least one ring atom which is N.

All of the embodiments for an N-heteroaryl described above for Formula I apply equally to an N-heteroaryl in Formula II.

In some embodiments of Formula II, at least one of $Ar^1$-$Ar^4$ is an S-heteroaryl having at least one ring atom which is S.

All of the embodiments for an S-heteroaryl described above for Formula I apply equally to an S-heteroaryl in Formula II.

In some embodiments of Formula II, at least one of $Ar^1$-$Ar^4$ is an O-heteroaryl having at least one ring atom that is O.

All of the embodiments for an O-heteroaryl described above for Formula I apply equally to an O-heteroaryl in Formula II.

In some embodiments of Formula II, at least one of $Ar^1$-$Ar^4$ is an N,O-heteroaryl having at least one ring atom that is N and at least one ring atom that is O.

All of the embodiments for an N,O-heteroaryl described above for Formula I apply equally to an N,O-heteroaryl in Formula II.

In some embodiments of Formula II, at least one of $Ar^1$-$Ar^4$ is an N,S-heteroaryl having at least one ring atom that is N and at least one ring atom that is S.

All of the embodiments for an N,S-heteroaryl described above for Formula I apply equally to an N,S-heteroaryl in Formula II.

In some embodiments of Formula II, at least one of $Ar^1$-$Ar^4$ is a hydrocarbon aryl.

In some embodiments, the hydrocarbon aryl has 6-30 ring carbons; in some embodiments, 6-20 ring carbons.

In some embodiments of Formula II, at least one of $Ar^1$-$Ar^4$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, and deuterated analogs thereof.

In some embodiments of Formula II, at least one of $Ar^1$-$Ar^4$ has Formula a, as described above.

In some embodiments of Formula II, at least one of $Ar^1$-$Ar^4$ has Formula b, as described above.

In some embodiments of Formula II, $Ar^1$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, and deuterated analogs thereof.

In some embodiments of Formula II, $Ar^1$ has Formula a.

In some embodiments of Formula II, $Ar^1$ has Formula b.

In some embodiments of Formula II, $Ar^2$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, and deuterated analogs thereof.

In some embodiments of Formula II, $Ar^2$ has Formula a.

In some embodiments of Formula II, $Ar^2$ has Formula b.

In some embodiments of Formula II, $Ar^3$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, and deuterated analogs thereof.

In some embodiments of Formula II, $Ar^3$ has Formula a.

In some embodiments of Formula II, $Ar^3$ has Formula b.

In some embodiments of Formula II, $Ar^4$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of fluoro, alkyl, alkoxy, silyl, siloxy, germyl, and deuterated analogs thereof.

In some embodiments of Formula II, $Ar^4$ has Formula a.

In some embodiments of Formula II, $Ar^4$ has Formula b.

In some embodiments of Formula II, any one or more of $Ar^1$-$Ar^4$ is substituted.

In some embodiments of Formula II, at least one of $Ar^1$-$Ar^4$ is substituted with a group selected from the group consisting of D, F, CN, alkyl, fluoroalkyl, aryl, heteroaryl, silyl, germyl, deuterated alkyl, deuterated partially-fluorinated alkyl, deuterated aryl, deuterated heteroaryl, deuterated silyl, and deuterated germyl.

In some embodiments, the compounds have Formula II-a:

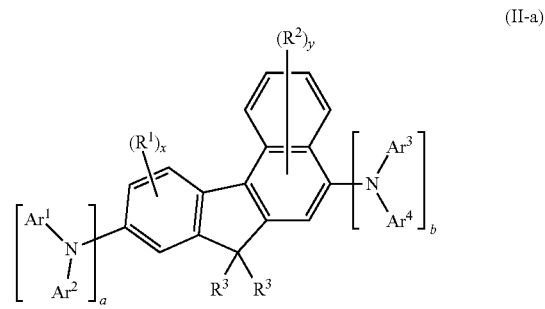

(II-a)

wherein:
$Ar^1$-$Ar^4$ are the same or different and are selected from the group consisting of hydrocarbon aryl, heteroaryl, and deuterated analogs thereof, with the proviso that at least one of $Ar^1$-$Ar^4$ is heteroaryl or deuterated heteroaryl;

$R^1$ and $R^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

a and b are the same or different and are 0 or 1, with the proviso that a+b≥1;

x is an integer of 0-4, with the proviso that when a=1, x=0-3; and y is an integer of 0-6, with the proviso that when b=1, y=0-5.

All of the embodiments for a, b, $Ar^1$, $Ar^2$, $Ar^3$, $Ar^4$, $R^1$, $R^2$, $R^3$, x, and y described above for Formula II apply equally to Formula II-a.

Examples of compounds having Formula II include, but are not limited to, the compounds shown below.

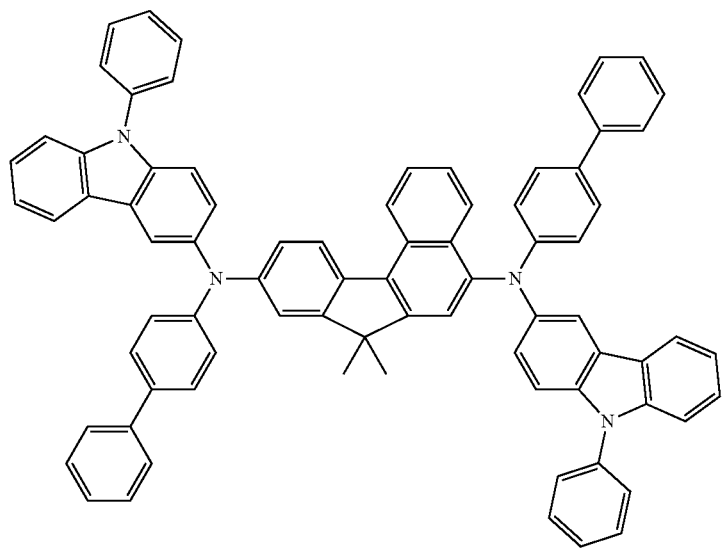
Compound II-1
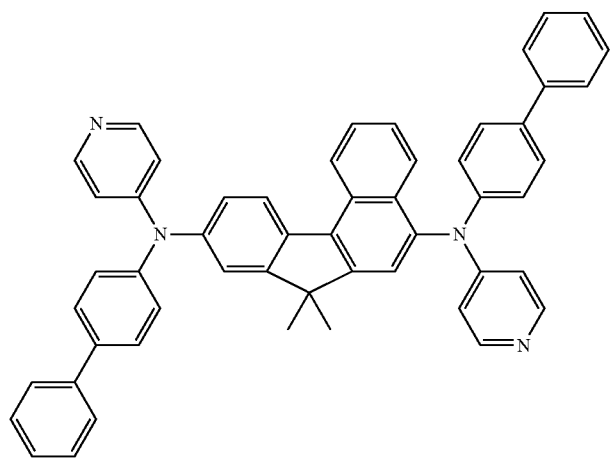
Compound II-2
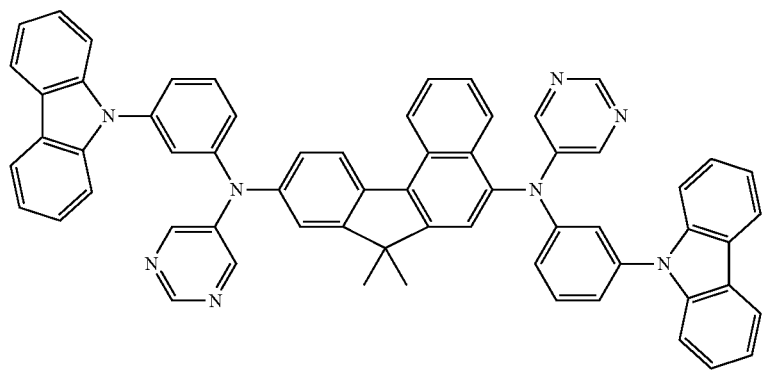
Compound II-3

-continued

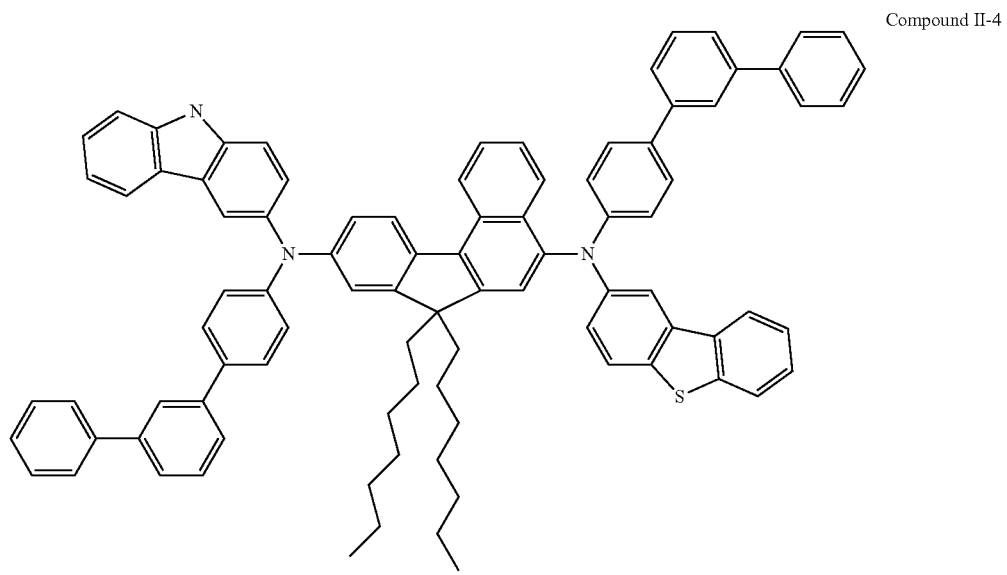

Compound II-4

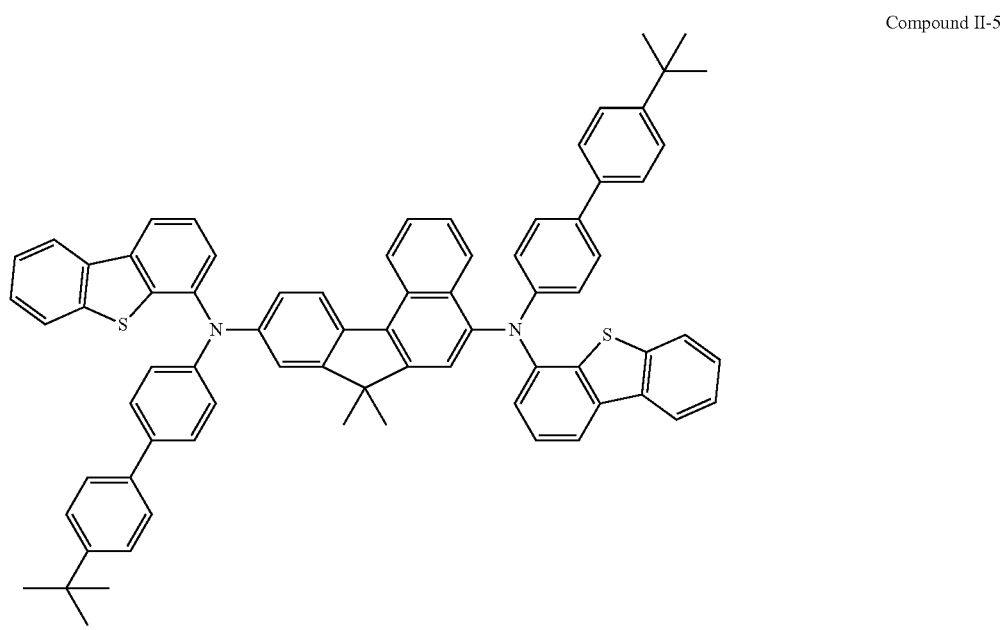

Compound II-5

5. Compounds Having Formula III or Formula III-a

The compounds of Formula III and Formula III-a have a benzofluorene core with two amino groups directly attached, wherein each amino nitrogen has two aryl groups attached.

The compounds having Formula III or Formula III-a have the core benzofluorene structure BzF-2, as described above.

In some embodiments, the new compounds have Formula III:

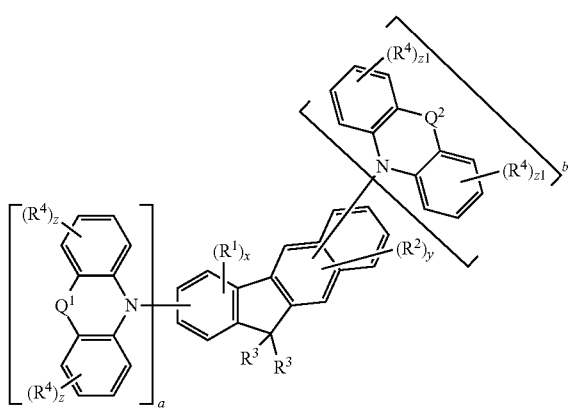

(III)

wherein:
- $Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;
- $R^1$, $R^2$, and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;
- $R^5$ is the same or different at each occurrence and is selected from the group consisting of H, D, F, alkyl, fluoroalkyl, deuterated alkyl, or deuterated partially-fluorinated alkyl;
- $R^6$ is selected from the group consisting of aryl and deuterated aryl;
- a and b are the same or different and are 0 or 1, with the proviso that a+b≥1;
- w is an integer of 1-6;
- x is an integer of 0-4, with the proviso that when a=1, x=0-3;
- y is an integer of 0-6, with the proviso that when b=1, y=0-5;
- z is an integer of 0-5, with the proviso that when $Q^1$ is not nil, z is 0-4; and
- z1 is an integer of 0-5, with the proviso that when $Q^2$ is not nil, z1 is 0-4.

All of the embodiments for a, b, $Q^1$, $Q^2$, $R^1$, $R^2$, $R^3$, $R^4$, $R^5$, $R^6$, w, x, y, z, and z1 described above for Formula I apply equally to Formula III.

In some embodiments of Formula III, a=1 and the amino nitrogen is bonded to position 1 on the benzofluorene core.
In some embodiments of Formula III, a=1 and the amino nitrogen is bonded to position 2 on the benzofluorene core.
In some embodiments of Formula III, a=1 and the amino nitrogen is bonded to position 3 on the benzofluorene core.
In some embodiments of Formula III, a=1 and the amino nitrogen is bonded to position 4 on the benzofluorene core.
In some embodiments of Formula III, b=1 and the amino nitrogen is bonded to position 5 on the benzofluorene core.
In some embodiments of Formula III, b=1 and the amino nitrogen is bonded to position 6 on the benzofluorene core.
In some embodiments of Formula III, b=1 and the amino nitrogen is bonded to position 7 on the benzofluorene core.
In some embodiments of Formula III, b=1 and the amino nitrogen is bonded to position 8 on the benzofluorene core.
In some embodiments of Formula III, b=1 and the amino nitrogen is bonded to position 9 on the benzofluorene core.
In some embodiments of Formula III, b=1 and the amino nitrogen is bonded to position 9 on the benzofluorene core.

In some embodiments, the compounds have Formula III-a:

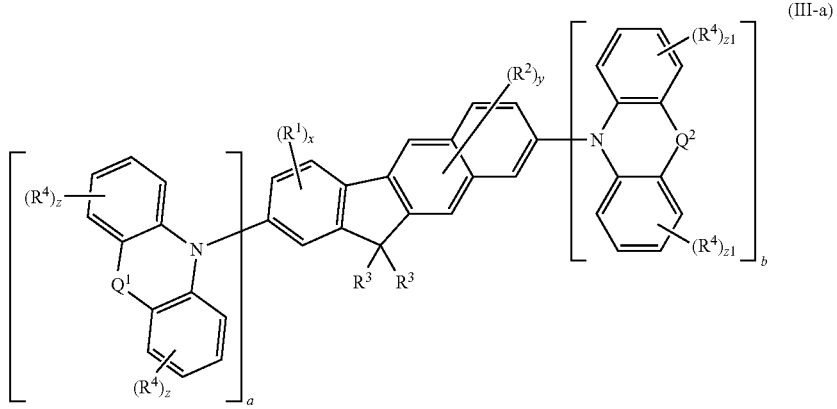

(III-a)

wherein:
- $Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;
- $R^1$, $R^2$, and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

$R^5$ is the same or different at each occurrence and is selected from the group consisting of H, D, F, alkyl, fluoroalkyl, deuterated alkyl, or deuterated partially-fluorinated alkyl;

$R^6$ is selected from the group consisting of aryl and deuterated aryl;

a and b are the same or different and are 0 or 1, with the proviso that a+b≥1;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when $Q^1$ is not nil, z is 0-4; and z1 is an integer of 0-5, with the proviso that when $Q^2$ is not nil, z1 is 0-4.

All of the embodiments for a, b, $Q^1$, $Q^2$, $R^1$, $R^2$, $R^3$, $R^4$, $R^5$, $R^6$, w, x, y, z, and z1 described above for Formula I apply equally to Formula III-a.

Any of the above embodiments of Formula III or Formula III-a can be combined with one or more of the other embodiments, so long as they are not mutually exclusive. For example, the embodiment in which $R^1$ is H or D can be combined with the embodiment where $R^3$ is an alkyl or deuterated alkyl having 3-8 carbons and the embodiment where a=b=1. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula III include, but are not limited to, the compounds shown below.

Compound III-1

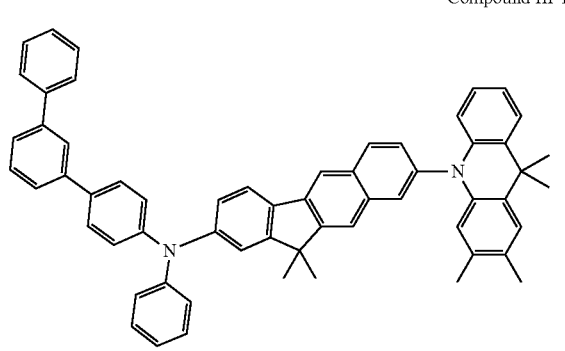

Compound III-2

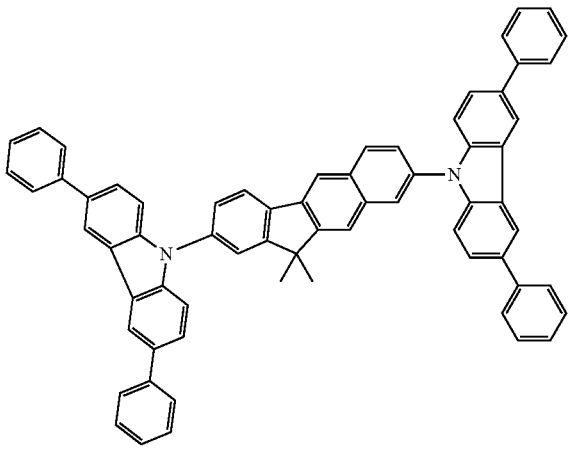

Compound III-3

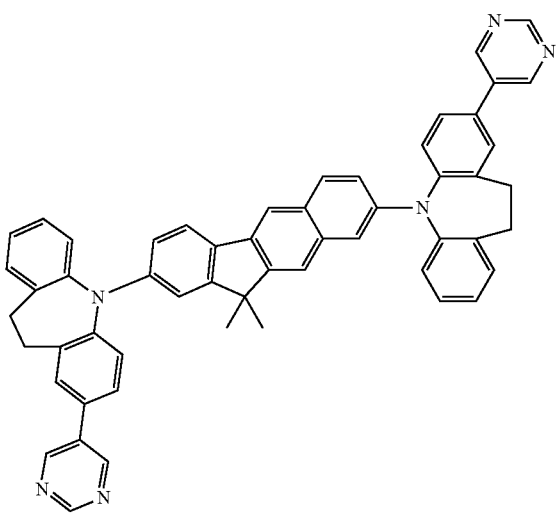

6. Compounds Having Formula IV or Formula IV-a

The compounds having Formula IV or Formula IV-a have the core benzofluorene structure BzF-2, described above.

In some embodiments, the compounds have Formula IV:

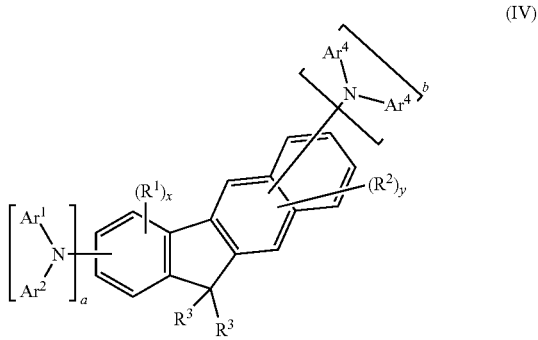

(IV)

wherein:
$Ar^1$-$Ar^4$ are the same or different and are selected from the group consisting of hydrocarbon aryl, heteroaryl, and deuterated analogs thereof, with the proviso that at least one of $Ar^1$-$Ar^4$ is heteroaryl or deuterated heteroaryl;

$R^1$ and $R^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

a and b are the same or different and are 0 or 1, with the proviso that a+b≥1;

x is an integer of 0-4, with the proviso that when a=1, x=0-3; and y is an integer of 0-6, with the proviso that when b=1, y=0-5.

In Formula IV, at least one of $Ar^1$-$Ar^4$ is heteroaryl or deuterated heteroaryl, and the heteroaryl ring is bonded directly to the amino nitrogen. When the heteroaryl group has two or more fused rings, the group is bonded directly to the amino nitrogen through any available position on any of the fused rings.

All of the embodiments for a, b, $Ar^1$, $Ar^2$, $Ar^3$, $Ar^4$, $R^1$, $R^2$, $R^3$, x, and y described above for Formula II apply equally to Formula IV.

In some embodiments of Formula IV, a=1 and the amino nitrogen is bonded to position 1 on the benzofluorene core.

In some embodiments of Formula IV, a=1 and the amino nitrogen is bonded to position 2 on the benzofluorene core.

In some embodiments of Formula IV, a=1 and the amino nitrogen is bonded to position 3 on the benzofluorene core.

In some embodiments of Formula IV, a=1 and the amino nitrogen is bonded to position 4 on the benzofluorene core.

In some embodiments of Formula IV, b=1 and the amino nitrogen is bonded to position 5 on the benzofluorene core.

In some embodiments of Formula IV, b=1 and the amino nitrogen is bonded to position 6 on the benzofluorene core.

In some embodiments of Formula IV, b=1 and the amino nitrogen is bonded to position 7 on the benzofluorene core.

In some embodiments of Formula IV, b=1 and the amino nitrogen is bonded to position 8 on the benzofluorene core.

In some embodiments of Formula IV, b=1 and the amino nitrogen is bonded to position 9 on the benzofluorene core.

In some embodiments of Formula IV, b=1 and the amino nitrogen is bonded to position 9 on the benzofluorene core.

In some embodiments, the compounds have Formula IV-a:

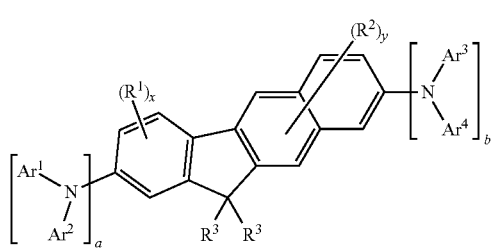

(IV-a)

wherein:

$Ar^1$-$Ar^4$ are the same or different and are selected from the group consisting of hydrocarbon aryl, heteroaryl, and deuterated analogs thereof, with the proviso that at least one of $Ar^1$-$Ar^4$ is heteroaryl or deuterated heteroaryl;

$R^1$ and $R^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

a and b are the same or different and are 0 or 1, with the proviso that a+b≥1;

x is an integer of 0-4, with the proviso that when a=1, x=0-3; and y is an integer of 0-6, with the proviso that when b=1, y=0-5.

All of the embodiments for a, b, $Ar^1$, $Ar^2$, $Ar^3$, $Ar^4$, $R^1$, $R^2$, $R^3$, x, and y described above for Formula II apply equally to Formula IV-a.

Any of the above embodiments of Formula IV or Formula IV-a can be combined with one or more of the other embodiments, so long as they are not mutually exclusive. For example, the embodiment in which $Ar^1$ is carbazole or deuterated carbazole can be combined with the embodiment where $Ar^2$ is phenyl or deuterated phenyl and the embodiment where $Ar^1$=$Ar^3$. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula IV include, but are not limited to, the compounds shown below.

Compound IV-1

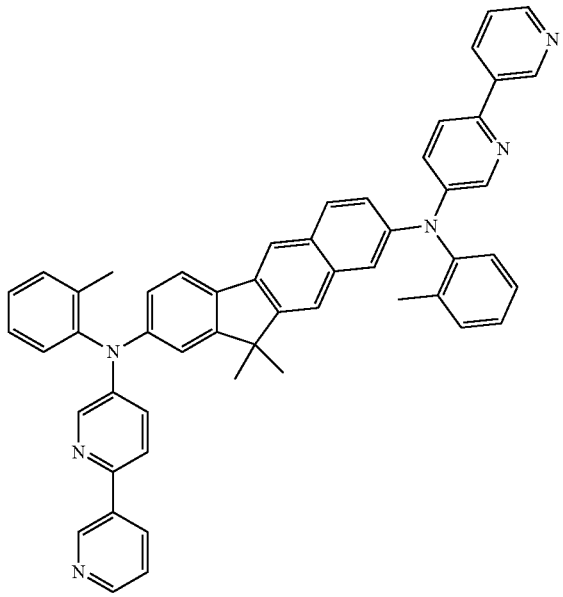

-continued

Compound IV-2

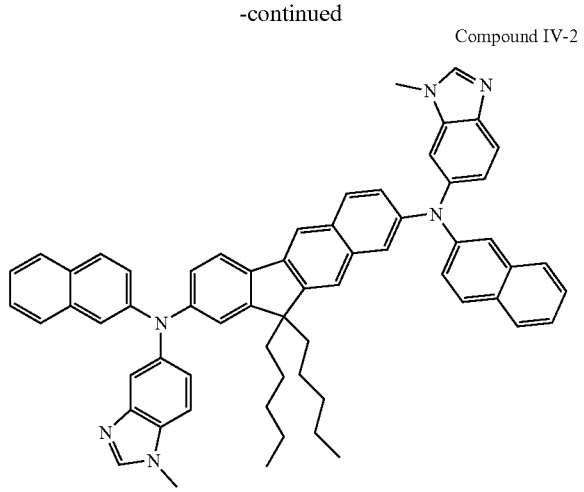

Compound IV-3

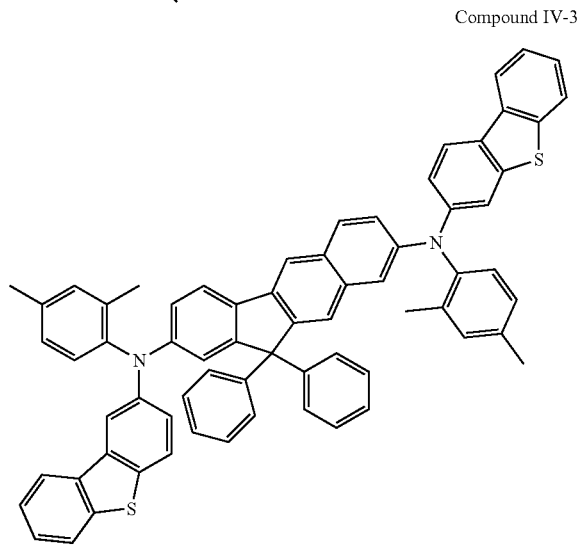

7. Compounds Having Formula V, Formula V-a, or Formula V-b

The compounds of Formula V, Formula V-a, and Formula V-b have a benzofluorene core with two amino groups directly attached, wherein each amino nitrogen has two aryl groups attached.

The compounds having Formula V, Formula V-a, or Formula V-b have the core benzofluorene structure BzF-3, described above In some embodiments, the compounds have Formula V:

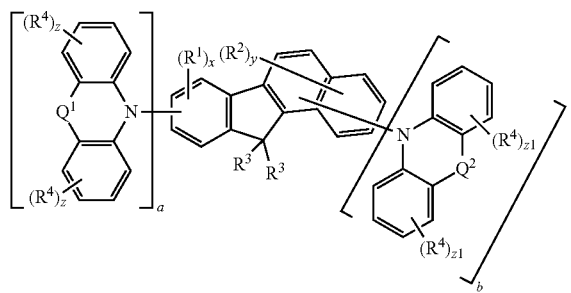

(V)

wherein:

$Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;

$R^1$, $R^2$, and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

$R^5$ is the same or different at each occurrence and is selected from the group consisting of H, D, F, alkyl, fluoroalkyl, deuterated alkyl, or deuterated partially-fluorinated alkyl;

$R^6$ is selected from the group consisting of aryl and deuterated aryl;

a and b are the same or different and are 0 or 1, with the proviso that a+b≥1;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when $Q^1$ is not nil, z is 0-4; and z1 is an integer of 0-5, with the proviso that when $Q^2$ is not nil, z1 is 0-4.

All of the embodiments for a, b, $Q^1$, $Q^2$, $R^1$, $R^2$, $R^3$, $R^4$, $R^5$, $R^6$, w, x, y, z, and z1 described above for Formula I apply equally to Formula V.

In some embodiments of Formula V, a=1 and the amino nitrogen is bonded to position 7 on the benzofluorene core.

In some embodiments of Formula V, a=1 and the amino nitrogen is bonded to position 8 on the benzofluorene core.

In some embodiments of Formula V, a=1 and the amino nitrogen is bonded to position 9 on the benzofluorene core.

In some embodiments of Formula V, a=1 and the amino nitrogen is bonded to position 10 on the benzofluorene core.

In some embodiments of Formula V, b=1 and the amino nitrogen is bonded to position 1 on the benzofluorene core.

In some embodiments of Formula V, b=1 and the amino nitrogen is bonded to position 2 on the benzofluorene core.

In some embodiments of Formula V, b=1 and the amino nitrogen is bonded to position 3 on the benzofluorene core.

In some embodiments of Formula V, b=1 and the amino nitrogen is bonded to position 4 on the benzofluorene core.

In some embodiments of Formula V, b=1 and the amino nitrogen is bonded to position 5 on the benzofluorene core.

In some embodiments of Formula V, b=1 and the amino nitrogen is bonded to position 6 on the benzofluorene core.

In some embodiments, the compounds have Formula V-a:

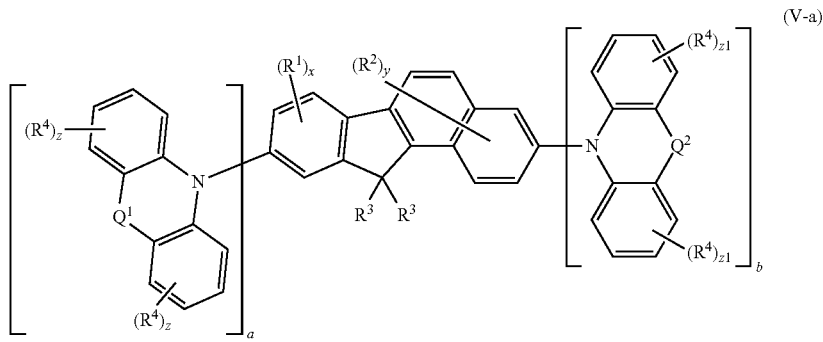

wherein:

- $Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;

- $R^1$, $R^2$, and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

- $R^5$ is the same or different at each occurrence and is selected from the group consisting of H, D, F, alkyl, fluoroalkyl, deuterated alkyl, or deuterated partially-fluorinated alkyl;

- $R^6$ is selected from the group consisting of aryl and deuterated aryl;

- a and b are the same or different and are 0 or 1, with the proviso that $a+b \geq 1$;

- w is an integer of 1-6;

- x is an integer of 0-4, with the proviso that when a=1, x=0-3;

- y is an integer of 0-6, with the proviso that when b=1, y=0-5;

- z is an integer of 0-5, with the proviso that when $Q^1$ is not nil, z is 0-4; and

- z1 is an integer of 0-5, with the proviso that when $Q^2$ is not nil, z1 is 0-4.

All of the embodiments for a, b, $Q^1$, $Q^2$, $R^1$, $R^2$, $R^3$, $R^4$, $R^5$, $R^6$, w, x, y, z, and z1 described above for Formula I apply equally to Formula V-a.

In some embodiments, the compounds have Formula V-b:

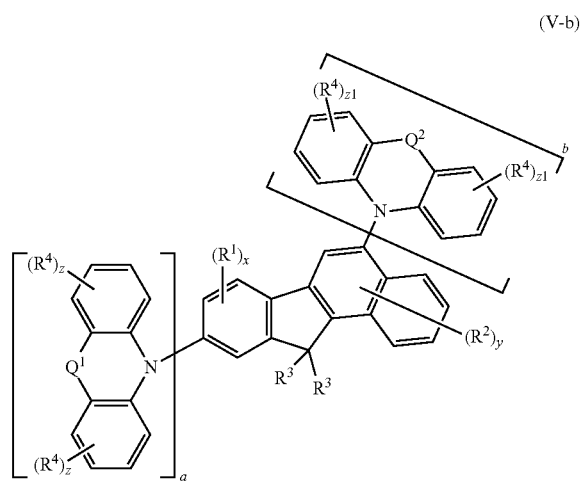

wherein:

- $Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;

- $R^1$, $R^2$, and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

- $R^5$ is the same or different at each occurrence and is selected from the group consisting of H, D, F, alkyl, fluoroalkyl, deuterated alkyl, or deuterated partially-fluorinated alkyl;

- $R^6$ is selected from the group consisting of aryl and deuterated aryl;

- a and b are the same or different and are 0 or 1, with the proviso that $a+b \geq 1$;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when $Q^1$ is not nil, z is 0-4; and z1 is an integer of 0-5, with the proviso that when $Q^2$ is not nil, z1 is 0-4.

All of the embodiments for a, b, $Q^1$, $Q^2$, $R^1$, $R^2$, $R^3$, $R^4$, $R^5$, $R^6$, w, x, y, z, and z1 described above for Formula I apply equally to Formula V-b.

Any of the above embodiments of Formula V, Formula V-a or Formula V-b can be combined with one or more of the other embodiments, so long as they are not mutually exclusive. For example, the embodiment in which at least one of $R^4$ is an N,O-heteroaryl can be combined with the embodiment where at least one $R^4$ has Formula b. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula V include, but are not limited to, the compounds shown below.

Compound V-1

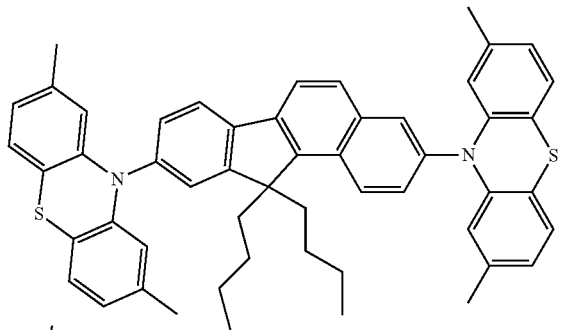

Compound V-2

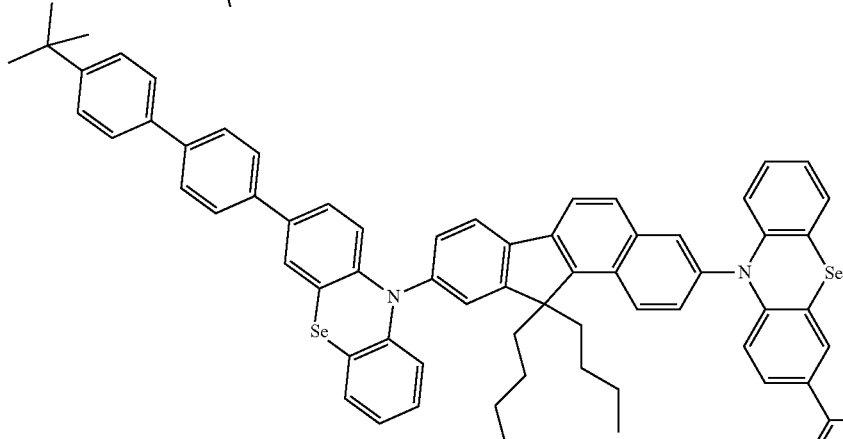

Compound V-3

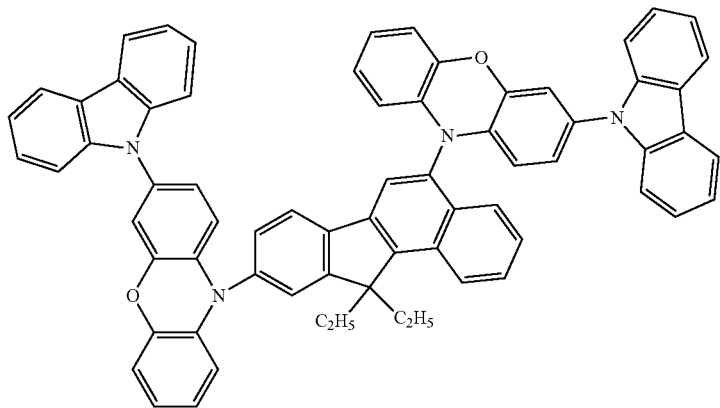

8. Compounds Having Formula VI, Formula VI-a or Formula VI-b

The compounds having Formula VI, Formula VI-a, or Formula VI-b have the core benzofluorene structure BzF-3, described above.

In some embodiments, the compounds have Formula VI:

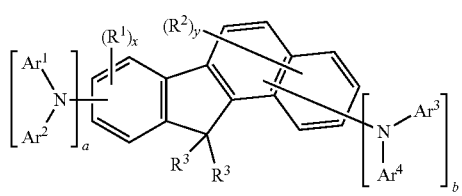

(VI)

wherein:
Ar$^1$-Ar$^4$ are the same or different and are selected from the group consisting of hydrocarbon aryl, heteroaryl, and deuterated analogs thereof, with the proviso that at least one of Ar$^1$-Ar$^4$ is heteroaryl or deuterated heteroaryl;
R$^1$ and R$^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
R$^3$ is the same or different at each occurrence and is selected from the group consisting of alkyl, silyl, germyl, aryl, and deuterated analogs thereof, where two alkyl R$^3$ groups can be joined together to make a cycloalkyl spiro ring, and where two R$^3$ phenyl groups can be joined to form a spiro fluorene group;
a and b are the same or different and are 0 or 1, with the proviso that a+b≥1;
x is an integer of 0-4, with the proviso that when a=1, x=0-3; and
y is an integer of 0-6, with the proviso that when b=1, y=0-5.

In Formula VI, at least one of Ar$^1$-Ar$^4$ is heteroaryl or deuterated heteroaryl, and the heteroaryl ring is bonded directly to the amino nitrogen. When the heteroaryl group has two or more fused rings, the group is bonded directly to the amino nitrogen through any available position on any of the fused rings.

In some embodiments of Formula VI, a=1 and the amino nitrogen is bonded to position 7 on the benzofluorene core.
In some embodiments of Formula VI, a=1 and the amino nitrogen is bonded to position 8 on the benzofluorene core.
In some embodiments of Formula VI, a=1 and the amino nitrogen is bonded to position 9 on the benzofluorene core.
In some embodiments of Formula VI, a=1 and the amino nitrogen is bonded to position 10 on the benzofluorene core.
In some embodiments of Formula VI, b=1 and the amino nitrogen is bonded to position 1 on the benzofluorene core.
In some embodiments of Formula VI, b=1 and the amino nitrogen is bonded to position 2 on the benzofluorene core.
In some embodiments of Formula VI, b=1 and the amino nitrogen is bonded to position 3 on the benzofluorene core.
In some embodiments of Formula VI, b=1 and the amino nitrogen is bonded to position 4 on the benzofluorene core.
In some embodiments of Formula VI, b=1 and the amino nitrogen is bonded to position 5 on the benzofluorene core.
In some embodiments of Formula VI, b=1 and the amino nitrogen is bonded to position 6 on the benzofluorene core.

All of the embodiments for a, b, Ar$^1$, Ar$^2$, Ar$^3$, Ar$^4$, R$^1$, R$^2$, R$^3$, x, and y described above for Formula II apply equally to Formula VI.

In some embodiments, the compounds have Formula VI-a:

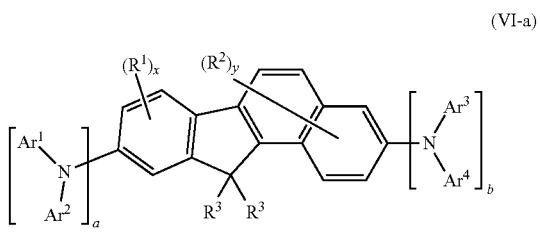

(VI-a)

wherein:
Ar$^1$-Ar$^4$ are the same or different and are selected from the group consisting of hydrocarbon aryl, heteroaryl, and deuterated analogs thereof, with the proviso that at least one of Ar$^1$-Ar$^4$ is heteroaryl or deuterated heteroaryl;
R$^1$ and R$^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
R$^3$ is the same or different at each occurrence and is selected from the group consisting of alkyl, silyl, germyl, aryl, and deuterated analogs thereof, where two alkyl R$^3$ groups can be joined together to make a cycloalkyl spiro ring, and where two R$^3$ phenyl groups can be joined to form a spiro fluorene group;
a and b are the same or different and are 0 or 1, with the proviso that a+b≥1;
x is an integer of 0-4, with the proviso that when a=1, x=0-3; and
y is an integer of 0-6, with the proviso that when b=1, y=0-5.

All of the embodiments for a, b, Ar$^1$, Ar$^2$, Ar$^3$, Ar$^4$, R$^1$, R$^2$, R$^3$, x, and y described above for Formula II apply equally to Formula VI-a.

In some embodiments, the compounds have Formula VI-b:

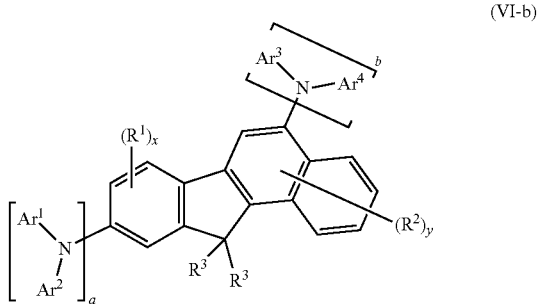

(VI-b)

wherein:
- $Ar^1$-$Ar^4$ are the same or different and are selected from the group consisting of hydrocarbon aryl, heteroaryl, and deuterated analogs thereof, with the proviso that at least one of $Ar^1$-$Ar^4$ is heteroaryl or deuterated heteroaryl;
- $R^1$ and $R^2$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;
- $R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;
- a and b are the same or different and are 0 or 1, with the proviso that a+b≥1;
- x is an integer of 0-4, with the proviso that when a=1, x=0-3; and
- y is an integer of 0-6, with the proviso that when b=1, y=0-5.

All of the embodiments for a, b, $Ar^1$, $Ar^2$, $Ar^3$, $Ar^4$, $R^1$, $R^2$, $R^3$, x, and y described above for Formula II apply equally to Formula VI-b.

Any of the above embodiments of Formula VI, Formula VI-a or Formula VI-b can be combined with one or more of the other embodiments, so long as they are not mutually exclusive. For example, the embodiment in which $Ar^1$ is dibenzothiophene or deuterated dibenzothiophene can be combined with the embodiment where x=1 and the embodiment where at least one $R^1$ is alkyl or deuterated alkyl. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula VI include, but are not limited to, the compounds shown below.

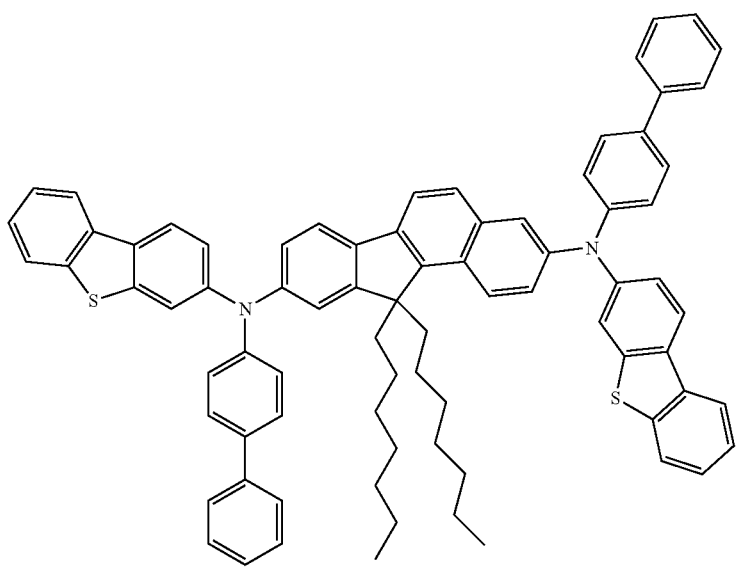

Compound VI-1

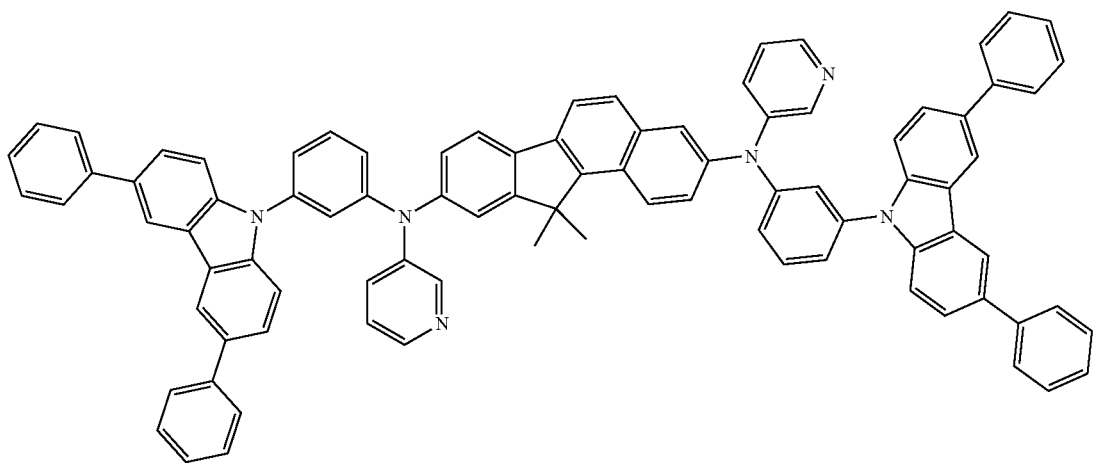

Compound VI-2

Compound VI-3

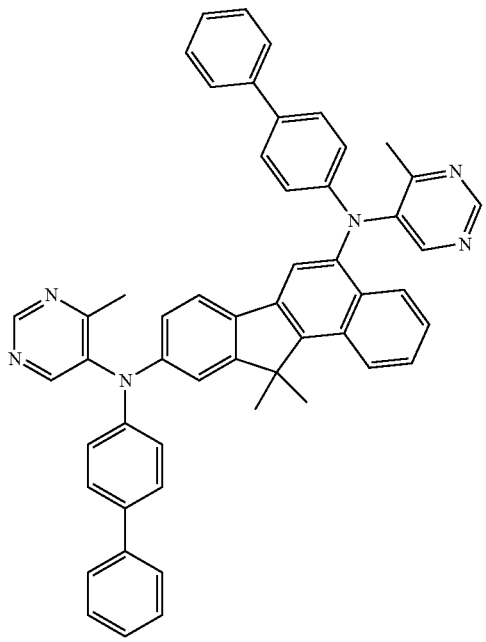

9. Devices

Organic electronic devices that may benefit from having one or more layers comprising the compounds having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that convert light of one wavelength to light of a longer wavelength, (e.g., a down-converting phosphor device); (5) devices that include one or more electronic components that include one or more organic semiconductor layers (e.g., a transistor or diode), or any combination of devices in items (1) through (5).

In some embodiments, the device includes a photoactive layer having a compound of Formula I.

In some embodiments, the device includes a photoactive layer having a compound of Formula I-a.

In some embodiments, the device includes a photoactive layer having a compound of Formula II.

In some embodiments, the device includes a photoactive layer having a compound of Formula II-a.

In some embodiments, the device includes a photoactive layer having a compound of Formula III.

In some embodiments, the device includes a photoactive layer having a compound of Formula III-a.

In some embodiments, the device includes a photoactive layer having a compound of Formula IV.

In some embodiments, the device includes a photoactive layer having a compound of Formula IV-a.

In some embodiments, the device includes a photoactive layer having a compound of Formula V.

In some embodiments, the device includes a photoactive layer having a compound of Formula V-a.

In some embodiments, the device includes a photoactive layer having a compound of Formula V-b.

In some embodiments, the device includes a photoactive layer having a compound of Formula VI.

In some embodiments, the device includes a photoactive layer having a compound of Formula VI-a.

In some embodiments, the device includes a photoactive layer having a compound of Formula VI-b.

In some embodiments, the device includes an anode and a cathode with a photoactive layer therebetween, where the photoactive layer includes a compound having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b.

One illustration of an organic electronic device structure including one of the new compounds described herein is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
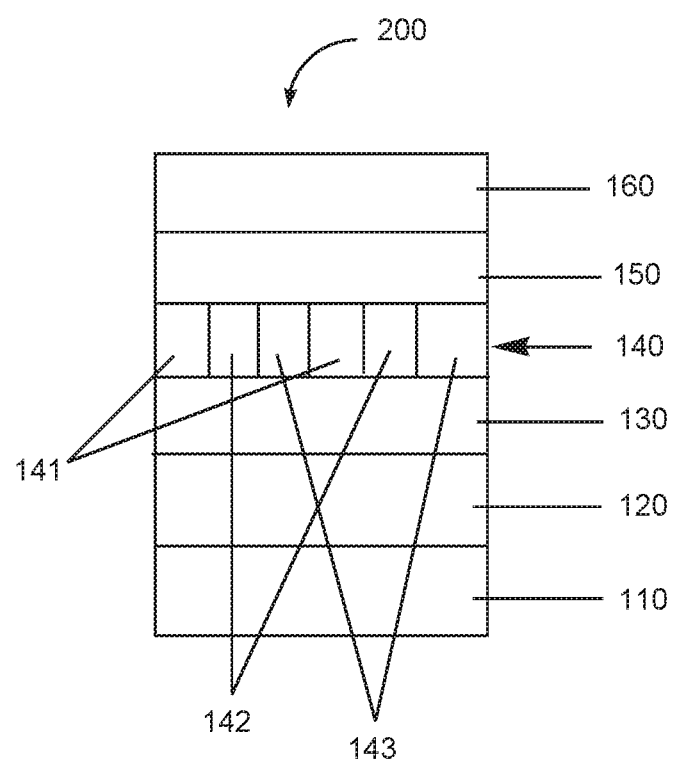
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-2000 Å, in some embodiments, 200-1000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b are useful as the emissive material in photoactive layer 140, having blue emission color. They can be used alone or as a dopant in a host material.

a. Photoactive Layer

In some embodiments, the photoactive layer includes a host material and a compound having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b as a dopant. In some embodiments, a second host material is present.

In some embodiments, the photoactive layer includes only a host material and a compound having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b as a dopant. In some embodiments, minor amounts of other materials, are present so long as they do not significantly change the function of the layer.

In some embodiments, the photoactive layer includes only a first host material, a second host material, and a compound having Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b as a dopant. In some embodiments, minor amounts of other materials, are present so long as they do not significantly change the function of the layer.

The weight ratio of dopant to total host material is in the range of 5:95 to 70:30; in some embodiments, 10:90 to 20:80.

In some embodiments, the host material is selected from the group consisting of anthracenes, chrysenes, pyrenes, phenanthrenes, triphenylenes, phenanthrolines, naphthalenes, triazines, quinolines, isoquinolines, quinoxalines, phenylpyridines, benzodifurans, metal quinolinate complexes, indolofluorenes, indolocarbazoles, indoloindoles, deuterated analogs thereof, and combinations thereof.

In some embodiments, the host material is a 9,10-diaryl anthracene compound or deuterated analog thereof.

In some embodiments, the host material is a chrysene derivative having one or two diarylamino substituents, or a deuterated analog thereof.

In some embodiments, the host material is an inodoloindole derivative having one or two diarylamino substituents, or a deuterated analog thereof.

Any of the compounds of Formula I, Formula I-a. Formula II, Formula II-a, Formula III, Formula III-a, Formula IV, Formula IV-a, Formula V, Formula V-a, Formula V-b, Formula VI, Formula VI-a, or Formula VI-b represented by the embodiments, specific embodiments, specific examples, and combination of embodiments discussed above can be used in the photoactive layer.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be made of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer can include charge transfer compounds, and the like, such as copper phthalocyanine and the tetrathiafulvalene-tetracyanoquinodimethane system (TTF-TCNQ).

In some embodiments, the hole injection layer includes a material selected from the group consisting of 1,4,5,8,9,12-hexaazatriphenylenehexacarbonitrile, tetracyanoquinodimethane, and tetracyano-2,3,5,6-tetrafluoroquinodimethane.

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for hole transport layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

In some embodiments, more than one hole transport layer is present (not shown).

Examples of electron transport materials which can be used for electron transport layer 150 include, but are not limited to, metal chelated oxinoid compounds, including metal quinolate derivatives such as tris(8-hydroxyquinolato) aluminum (AlQ), bis(2-methyl-8-quinolinolato)(p-phenylphenolato) aluminum (BAlq), tetrakis-(8-hydroxyquinolato) hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; fluoranthene derivatives, such as 3-(4-(4-methylstyryl)phenyl-p-tolylamino)fluoranthene; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of blue luminance by the electron transport layer. To prevent energy transfer quenching, the singlet energy of the anti-quenching material has to be higher than the singlet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

In some embodiments, the device is fabricated by liquid deposition of the hole injection layer, and by vapor deposition of the hole transport layer, the photoactive layer, the anode, the electron transport layer, an electron injection layer and the cathode.

In some embodiments, the device is fabricated by vapor deposition of all the layers.

In some embodiments, the hole injection layer is formed by liquid deposition. The hole injection layer can be deposited from any liquid medium in which it is dissolved or dispersed and from which it will form a film. In some embodiments, the liquid medium includes only one or more organic solvents. In some embodiments, minor amounts of other materials are present, so long as they do not substantially affect the liquid medium.

In some embodiments, the liquid medium includes only water or includes only water and an organic solvent. In some embodiments, minor amounts of other materials are present, so long as they do not substantially affect the liquid medium.

The hole injection material is present in the liquid medium in an amount from 0.5 to 10 percent by weight.

In some embodiments, the hole injection layer is formed by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

In some embodiments, the hole injection layer is formed by vapor deposition. Such techniques are well known in the art.

In some embodiments, the hole transport layer is formed by liquid deposition of hole transport material in a liquid medium. The liquid medium is one in which the hole transport material is dissolved or dispersed and from which it will form a film. In some embodiments, the liquid medium includes one or more organic solvents. In some embodiments, the liquid medium includes water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

In some embodiments, the hole transport layer is formed by vapor deposition. Such techniques are well known in the art.

In some embodiments, the photoactive layer is formed by liquid deposition of the photoactive material and one or more host materials in a liquid medium. The liquid medium is one in which the materials of the photoactive layer are dissolved or dispersed and from which it will form a film. In some embodiments, the liquid medium includes one or more organic solvents. In some embodiments, minor amounts of additional materials are present so long as they do not substantially affect the function of the photoactive layer.

Suitable classes of solvents include, but are not limited to, aliphatic hydrocarbons (such as decane and hexadecane), halogenated hydrocarbons (such as methylene chloride, chloroform, chlorobenzene, and perfluoroheptane), aromatic hydrocarbons (such as non-substituted and alkyl- and alkoxy-substituted toluenes and xylenes), aromatic ethers (such as anisole and dibenzyl ether), heteroaromatics (such as pyridine) polar solvents (such as tetrahydropyran ("THP"), dimethylacetamide ("DMAC") and N-methyl pyrrolidone ("NMP")), esters (such as ethylacetate, propylene carbonate, methyl benzoate), alcohols and glycols (such as isopropanol and ethylene glycol), glycol ethers and derivatives (such as propylene glycol methyl ether and propylene glycol methyl ether acetate), and ketones (such as cyclopentanone and diisobutyl ketone).

The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

In some embodiments, the photoactive layer is formed by vapor deposition. Such techniques are well known in the art.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Example 1

This example illustrates the preparation of a compound having Formula I, Compound I-1, 10,10'-(7,7-dimethyl-7H-benzo[c]fluorene-5,9-diyl)bis(9,9-dimethyl-9,10-dihydroacridine)

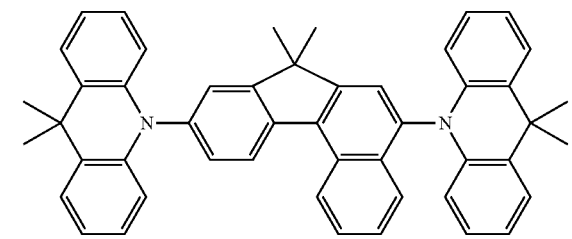

To a 250 mL round bottom flask, equipped with stir bar, condensing column and heating block inside a drybox, were added 5,9-dibromo-7,7-dimethyl-7H-benzo[c]fluorene (5.21 g, 10 mmol), 9,9-dimethyl-9,10-dihydroacridine (4.39 g, 21 mmol), Pd(OAc)$_2$ (366 mg, 0.4 mmol), P(tBu)$_3$ (90 mg, 1.6 mmol) and toluene (110 mL). This was stirred for a minute before adding the NaOtBu (324 mg, 22 mmol) in small portions. The reaction was stirred at 45° C. in drybox overnight. UPLC analysis indicated that all starting dibromide had been consumed with product formed in >95% conversion. This was removed from the drybox, passed through a layer of Celite and a layer of silica gel eluted with toluene (50 mL). This was removed of solvent to give a brown color solid material. The crude product was re-dissolved in DCM (20 mL) and separated on a Silica gel column eluted with DCM. The product containing fractions were collected and the solvent was evaporated. The material was further purified by passing through a short Alumina column eluted with DCM/hexane, crystallized 3 times from DCM/CH$_3$CN to give 3.1 g of white crystalline material in 99.9% purity.

Synthesis Example 2

This example illustrates the preparation of a compound having Formula I, Compound I-4, 5-(3,6-di-tert-butyl-9H-carbazol-9-yl)-N,N-bis(3,5-dimethylphenyl)-7,7-dimethyl-7H-benzo[c]fluoren-9-amine Step 1.
N-(2,4-dimethylphenyl)-3-methylbiphenyl-4-amine

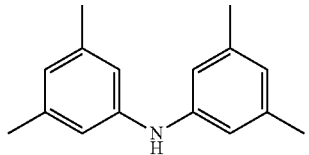

To an 1000 mL round bottom flask, equipped with stir bar, condensing column and heating block inside a drybox, were added 1-bromo-3,5-dimethylbenzene (25.0 g, 135 mmol), 3,5-dimethylaniline (17.2 g, 142 mmol), Pd$_2$(DBA)$_3$ (2.47 g, 2.7 mmol), P(tBu)$_3$ (1.1 g, 5.4 mmol) and toluene (305 mL). This was stirred for a minute before adding the NaOtBu (14.3 g, 148.6 mmol) in small portions. The reaction was stirred at room temperature for 1 hour and was shown complete by UPLC analysis. This was removed from the drybox, passed through a layer of Celite and a layer of silica gel with toluene (100 mL). This was removed of solvent, dissolved in DCM/hexane (1/9 30 mL) and passed through a short Silica gel column (5×10 cm), eluted with hexane first, then with DCM/hexane (1/7). Fractions were identified by TLC, collected, and the solvent was removed by rotary evaporation. The product was obtained as colorless thick oil that solidified on standing at RT overnight. Yield, 27 g in 99.0% purity by UPLC analysis.

Step 2. 5-bromo-N,N-bis(3,5-dimethylphenyl)-7,7-dimethyl-7H-benzo[c]fluoren-9-amine

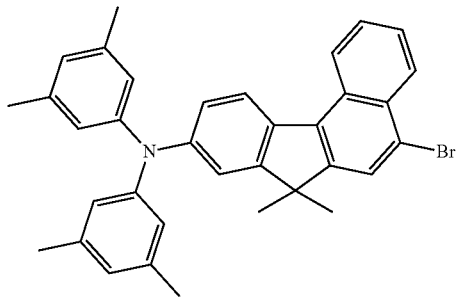 [SMILES: Cc1cc(C)cc(N(c2cc(C)cc(C)c2)c2ccc3c(c2)C(C)(C)c2cc(Br)c4ccccc4c2-3)c1]

To an 250 mL round bottom flask, equipped with stir bar, condensing column and heating block inside a drybox, were added 5-bromo-9-iodo-7,7-dimethyl-7H-benzo[c]fluorene (4.53 g, 10 mmol), bis(3,5-dimethylphenyl)amine (2.32 g, 10.1 mmol), Pd$_2$(DBA)$_3$ (183 mg, 0.2 mmol), DPPF (222 mg, 0.4 mmol) and toluene (100 mL). This was stirred for a minute before adding the NaOtBu (1.15 g, 12 mmol) in small portions. This was stirred at 90° C. for 4 hours. After cooling to RT, the reaction was removed from the drybox, passed through a layer of Celite and a layer of silica gel with toluene (100 mL). This was removed of solvent and the crude product was purified by chromatograph on a Silica gel column (CombiClush) eluted by chloroform/hexane gradient. The Product was obtained as a light-brown amorphous material, 3.18 g in 99.6% purity.

Step 3. 5-(3,6-di-tert-butyl-9H-carbazol-9-yl)-N,N-bis(3,5-dimethylphenyl)-7,7-dimethyl-7H-benzo[c]fluoren-9-amine

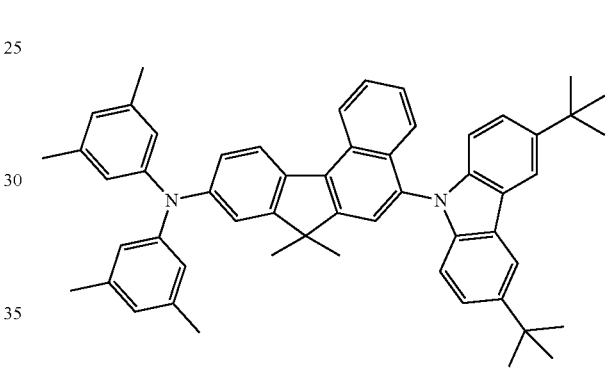

To an 250 mL round bottom flask, equipped with stir bar, condensing column and heating block inside a drybox, were added 5-bromo-N,N-bis(3,5-dimethylphenyl)-7,7-dimethyl-7H-benzo[c]fluoren-9-amine (2.76 g, 5.0 mmol), 3,6-di-tert-butyl-9H-carbazole (1.42 g, 5.05 mmol), Pd$_2$(DBA)$_3$ (923 mg, 0.1 mmol), P(tBu)$_3$ (40 mg, 0.2 mmol) and o-xylene (75 mL). This was stirred for a minute before adding the NaOtBu (577 g, 6.0 mmol) in small portions. The reaction was stirred with under gentle refluxing overnight. UPLC analysis indicated that all starting bromide had been consumed with the product as the major component. After cooling, this was removed from the drybox, passed through a layer of Celite and a layer of silica gel eluted with toluene (60 mL). This was removed of solvent to give a brown color solid material. The crude product was purified by chromatograph on a Silica gel column (CombiClush) eluted by chloroform/hexane gradient. The Product was obtained as a light-yellow amorphous material, 1.54 g in 99.9% purity by UPLC analysis.

Synthesis Example 3

This example illustrates the preparation of a compound having Formula I, Compound I-5, 9-(3,6-di-tert-butyl-9H-carbazol-9-yl)-N,N-bis(3,5-dimethylphenyl)-7,7-dimethyl-7H-benzo[c]fluoren-5-amine Step 1. 9-bromo-N,N-bis(3,5-dimethylphenyl)-7,7-dimethyl-7H-benzo[c]fluoren-5-amine

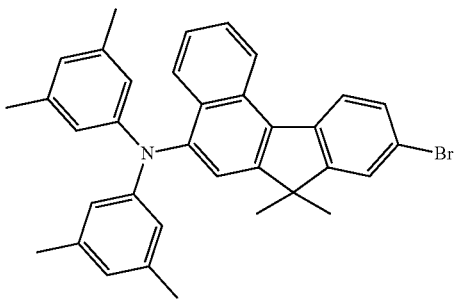 [SMILES: Cc1cc(C)cc(N(c2cc(C)cc(C)c2)c2cc3c(c4ccccc24)-c2ccc(Br)cc2C3(C)C)c1]

To an 250 mL round bottom flask, equipped with stir bar, condensing column and heating block inside a drybox, were added 5,9-dibromo-7,7-dimethyl-7H-benzo[c]fluorene (4.06 g, 10 mmol), bis(3,5-dimethylphenyl)amine (2.32 g, 10.1 mmol), Pd$_2$(DBA)$_3$ (183 mg, 0.2 mmol), DPPF (222 mg, 0.4 mmol) and toluene (100 mL). This was stirred for a minute before adding the NaOtBu (1.15 g, 12 mmol) in small portions. This was stirred at room temperature overnight. The reaction was shown complete by UPLC. After cooling to RT, the reaction was removed from the drybox, passed through a layer of Celite and a layer of silica gel with toluene (100 mL). This was removed of solvent and the crude product was purified by chromatograph on a Silica gel column (CombiClush) eluted by chloroform/hexane gradient. The product was crystallized from hexane, 1.07 g in 99.6%, 2nd crop, 0.2 g, 99.1%, 3rd crop, 0.4 g, 98.4% and 1.06 g, 90% by UPLC analysis.

Step 2. 5-(3,6-di-tert-butyl-9H-carbazol-9-yl)-N,N-bis(3,5-dimethylphenyl)-7,7-dimethyl-7H-benzo[c]fluoren-9-amine

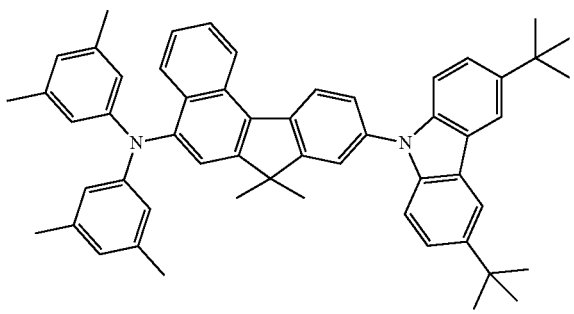 [SMILES: Cc1cc(C)cc(N(c2cc(C)cc(C)c2)c2cc3c(c4ccccc24)-c2ccc(-n4c5ccc(C(C)(C)C)cc5c5cc(C(C)(C)C)ccc54)cc2C3(C)C)c1]

To an 100 mL round bottom flask, equipped with stir bar, condensing column and heating block inside a drybox, were added 9-bromo-N,N-bis(3,5-dimethylphenyl)-7,7-dimethyl-7H-benzo[c]fluoren-5-amine (1.05 g, 1.91 mmol), 3,6-di-tert-butyl-9H-carbazole (567 mg, 2.00 mmol), Pd$_2$(DBA)$_3$ (52 mg, 0.06 mmol), P(tBu)$_3$ (23 mg, 0.11 mmol) and o-xylene (50 mL). This was stirred for a minute before adding the NaOtBu (238 mg, 2.48 mmol) in small portions. The reaction was stirred with under gentle refluxing overnight. UPLC analysis indicated that all starting bromide had been consumed with the product formed as the major component. After cooling, this was removed from the drybox, passed through a layer of Celite and a layer of silica gel eluted with toluene (60 mL). This was removed of solvent to give a brown color solid material. The crude product was purified by chromatograph on a Silica gel column (CombiClush) eluted by chloroform/hexane gradient. The product was crystallized from toluene/heptane to give a pale yellow crystalline material, 0.8 g in 99.9% purity by UPLC analysis.

Device Examples (1) Materials
ET-1 is an aryl phosphine oxide.
ET-2 is lithium quinolate.
HIJ-1 is a hole injection material which is made from an aqueous dispersion of an electrically conductive polymer and a polymeric fluorinated sulfonic acid. Such materials have been described in, for example, U.S. Pat. No. 7,351,358.
HIJ-2 is 1,4,5,8,9,12-hexaazatriphenylenehexacarbonitrile.
Host H1 is a deuterated diaryl anthracene. The compound can be made using known C—C coupling techniques. Such materials have been described in published PCT Application WO 2011028216
HTM-1 is a triarylamine polymer. The polymer can be made using known C—C and C—N coupling techniques. Such materials have been described in, for example, published PCT Application WO 2011159872.
HTM-2 is an aromatic compound having multiple phenyl groups. The compound can be made using known C—C coupling techniques. Such materials have been described in, for example, published PCT Application WO 2015089304.

(2) Device Fabrication
OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of hole transport material in a solvent of anisole:1-methyl-2-pyrrolindone:cyclohexylbenzene (96:3:1, by volume), and then heated to remove solvent. After cooling the substrates were spin-coated with a methyl benzoate solution of the host and dopant, and heated to remove solvent. The substrates were masked and placed in a vacuum chamber. A layer of electron transport material was deposited by thermal evaporation, followed by a layer of electron injection material. Masks were then changed in vacuo and a layer of Al was deposited by thermal evaporation. The chamber was vented, and the devices were encapsulated using a glass lid, dessicant, and UV curable epoxy.

(3) Device Characterization
The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Examples 1-3

These examples illustrate the use of a material having Formula I, Compound I-4, as the photoactive dopant in a device. The devices had the following layers.
Anode=ITO (50 nm)
HIL=HIJ-1 (42 nm)
HTL=HTM-1:HTM-2 (3:2) (18 nm)
EML=H1 and Compound I-4, in the weight ratios given below (38 nm)
ETL=ET-1:ET-2 (2:3) (20 nm)
Cathode=Al (100 nm)
The results are given in Table 3 below.

TABLE 3

Device results

| Ex. | Ratio | CE (cd/A) | EQE (%) | CIE (x, y) | V at 15 mA/cm$^2$ |
|---|---|---|---|---|---|
| 1 | 93:7 | 3.5 | 4.4 | 0.147, 0.084 | 4.3 |
| 2 | 96:4 | 3.1 | 4.0 | 0.147, 0.082 | 4.3 |
| 3 | 98:2 | 2.6 | 3.4 | 0.147, 0.081 | 4.3 |

All data at 1000 nits. Ratio is the weight ratio of host H1 to dopant compound; CE is the current efficiency; EQE=external quantum efficiency; CIE(x,y) refers to the x and y color coordinates according to the C.I.E. chromaticity scale (Commission Internationale de L'Eclairage, 1931).

Device Examples 4-5

These examples illustrate the use of a material having Formula I, Compound I-5, as the photoactive dopant in a device.

The devices had the same structure as in Device Examples 1-3, except that Compound I-5 was used in place of Compound I-4. The ratios and the devices results are given in Table 4 below.

TABLE 4

Device results

| Ex. | Ratio | CE (cd/A) | EQE (%) | CIE (x, y) | V at 15 mA/cm$^2$ |
|---|---|---|---|---|---|
| 4 | 93:7 | 4.8 | 4.8 | 0.141, 0.119 | 4.4 |
| 5 | 96:4 | 4.0 | 4.2 | 0.142, 0.112 | 4.4 |

All data at 1000 nits. Ratio is the weight ratio of host H1 to dopant compound; CE is the current efficiency; EQE=external quantum efficiency; CIE(x,y) refers to the x and y color coordinates according to the C.I.E. chromaticity scale (Commission Internationale de L'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula I, Formula II, Formula III, Formula IV, Formula V, or Formula VI:

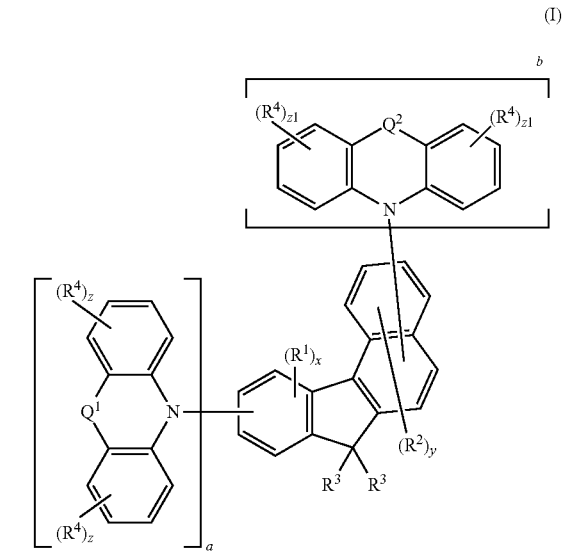

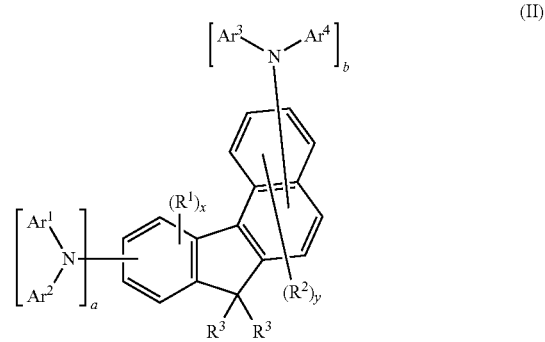

-continued (III)

(IV)

(V)

(VI)

wherein:
Ar¹ and Ar⁴ are the same or different and are heteroaryl or deuterated heteroaryl, Ar² and Ar³ are the same or different and are hydrocarbon aryl, and where Ar¹-Ar⁴ can be substituted with a group selected from the group consisting of D, F, CN, alkyl, fluoroalkyl, aryl, N-heteroaryl, silyl, germyl, deuterated alkyl, deuterated partially-fluorinated alkyl, deuterated aryl, deuterated heteroaryl, deuterated silyl, and deuterated germyl;

$Q^1$ and $Q^2$ are the same or different and are selected from the group consisting of nil, a single bond connecting the two aryl groups on the nitrogen, $(CR^5{}_2)_w$, $NR^6$, O, S, and Se, with the proviso that at least one of $Q^1$ and $Q^2$ is not nil;

$R^1$, $R^2$ and $R^4$ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

$R^3$ is the same or different at each occurrence and is selected from the group consisting of alkyl, silyl, germyl, aryl, and deuterated analogs thereof, where two alkyl $R^3$ groups can be joined together to make a cycloalkyl spiro ring, and where two $R^3$ phenyl groups can be joined to form a spiro fluorene group;

$R^5$ is the same or different at each occurrence and is selected from the group consisting of H, D, F, alkyl, fluoroalkyl, deuterated alkyl, or deuterated partially-fluorinated alkyl;

$R^6$ is selected from the group consisting of aryl and deuterated aryl;

a and b are the same or different and are 0 or 1, with the proviso that a+b≥1, and with the proviso that when a=1 and b=0, Q1 is not a single bond, and, in Formula V, with the proviso that when a=1 and b=0, Q1 is not $NR_6$;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when $Q^1$ is not nil, z is 0-4; and z1 is an integer of 0-5, with the proviso that when $Q^2$ is not nil, z1 is 0-4.

2. The compound of claim 1 having Formula I-a (I-a)

3. The compound of claim 1 having Formula II-a

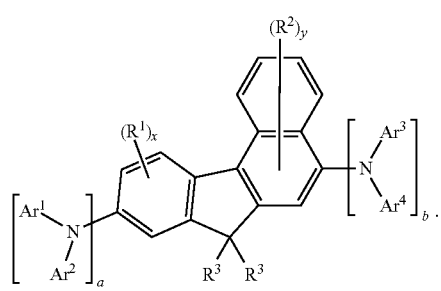

(II-a)

4. The compound of claim 1, wherein at least one of $Q^1$ and $Q^2$ is a single bond.

5. The compound of claim 1, wherein at least one of $Q^1$ and $Q^2$ is $(CR^5{}_2)$.

6. The compound of claim 1, wherein x=y=0.

7. The compound of claim 1, wherein x>0 and at least one $R^1$ is D.

8. The compound of claim 1, wherein y>0 and at least one $R^2$ is D.

9. The compound of claim 1, wherein $R^3$ is selected from the group consisting of alkyl and deuterated alkyl having 1-12 carbons.

10. The compound of claim 1, wherein at least one of $Ar^1$-$Ar^4$ is an N-heteroaryl selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, indole, indoloindole, substituted derivatives thereof, and deuterated analogs thereof.

11. The compound of claim 10, wherein the N-heteroaryl is a carbazole or deuterated carbazole.

12. The compound of claim 1, wherein a=b=1.

13. The compound of claim 1, wherein the N-heteroaryl is selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, indole, indoloindole, substituted derivatives thereof, and deuterated analogs thereof.

14. The compound of claim 1, wherein the compound is selected from the group consisting of following compounds:

Compound I-1 BD3501

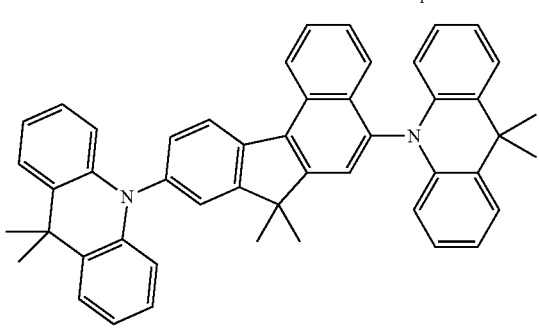

Compound I-2

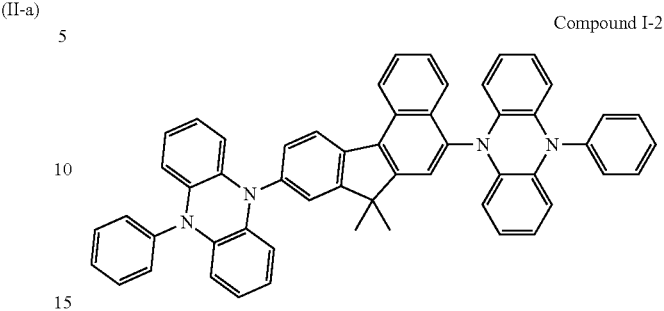

Compound I-3

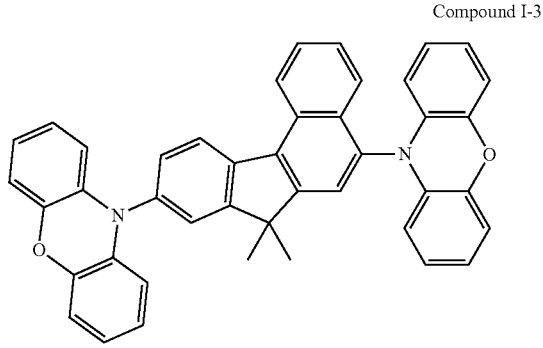

Compound I-4 (BD3839)

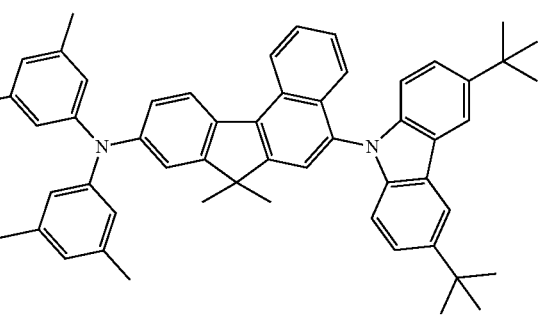

Compound I-5 (BD3847)

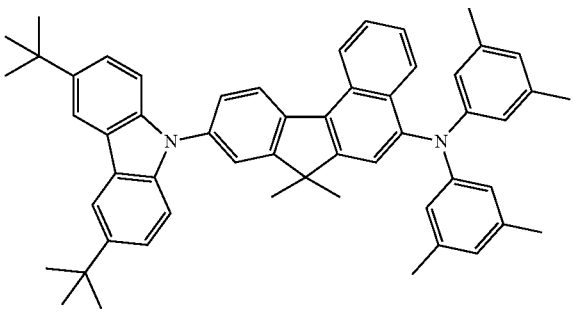

Compound II-1
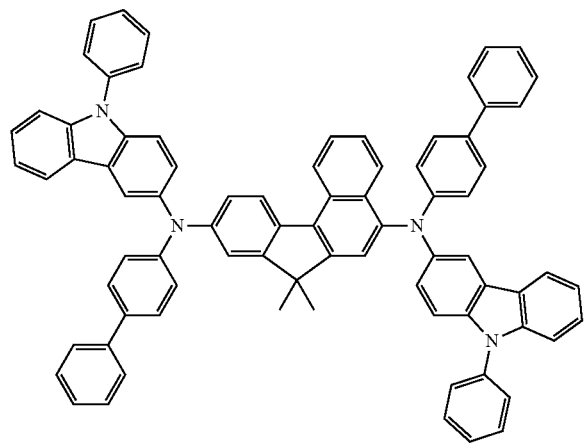
Compound II-2
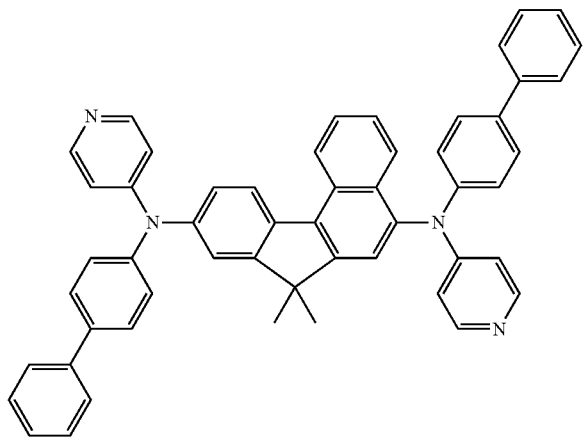
Compound II-3
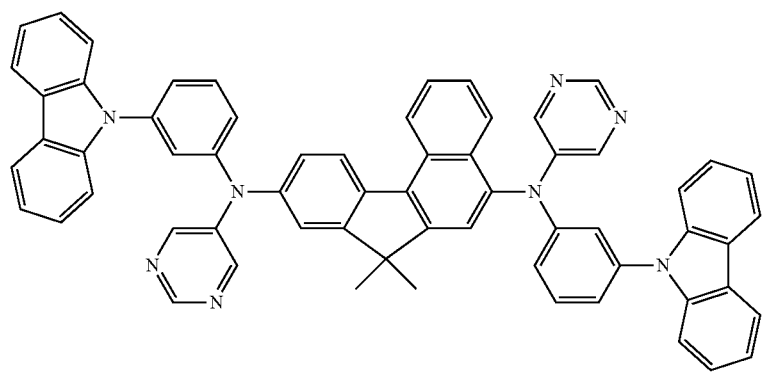
Compound II-4
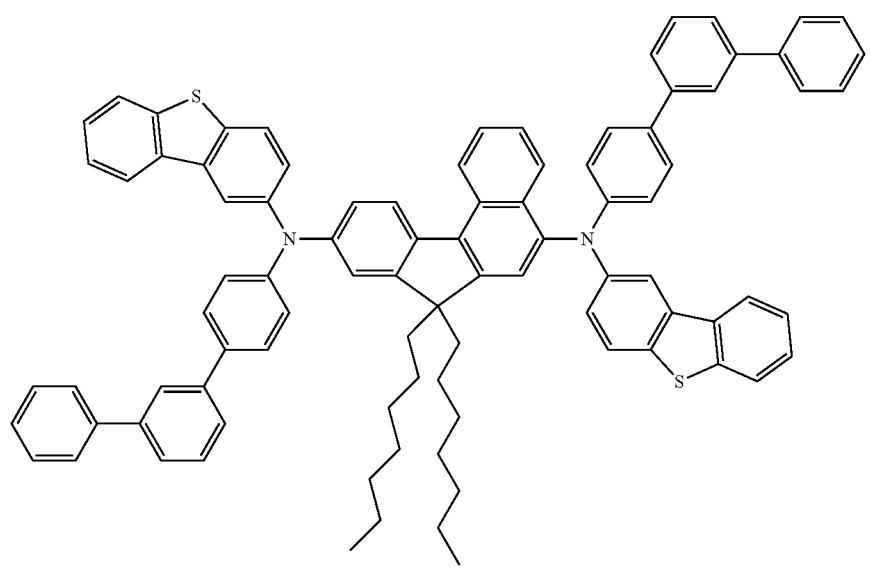

-continued
Compound II-5
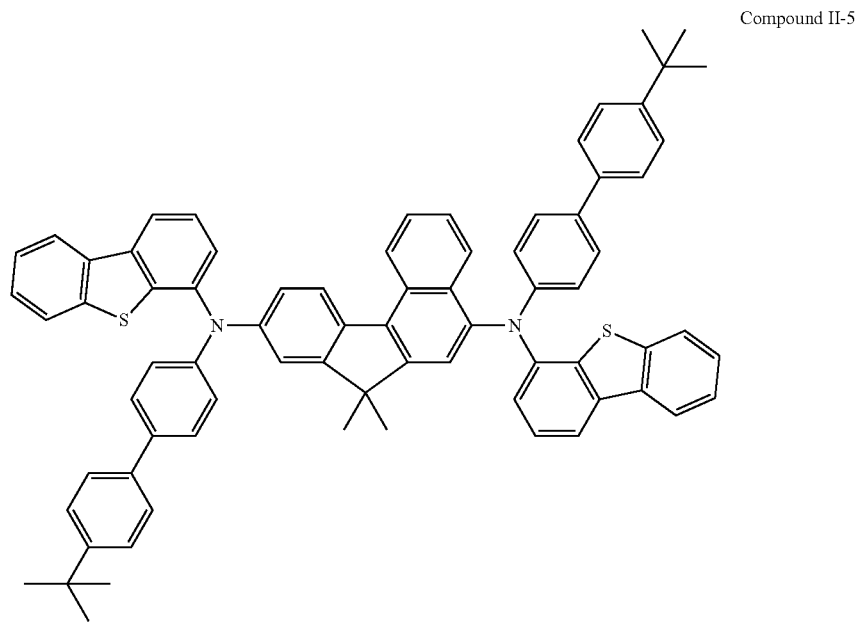 [SMILES: CC(C)(C)c1ccc(-c2ccc(N(c3ccc4c(c3)C(C)(C)c3cc(N(c5ccc(-c6ccc(C(C)(C)C)cc6)cc5)c5cccc6c5sc5ccccc56)c5ccccc5c3-4)c3cccc4c3sc3ccccc34)cc2)cc1]
-continued
Compound III-1
Compound III-2
Compound III-3
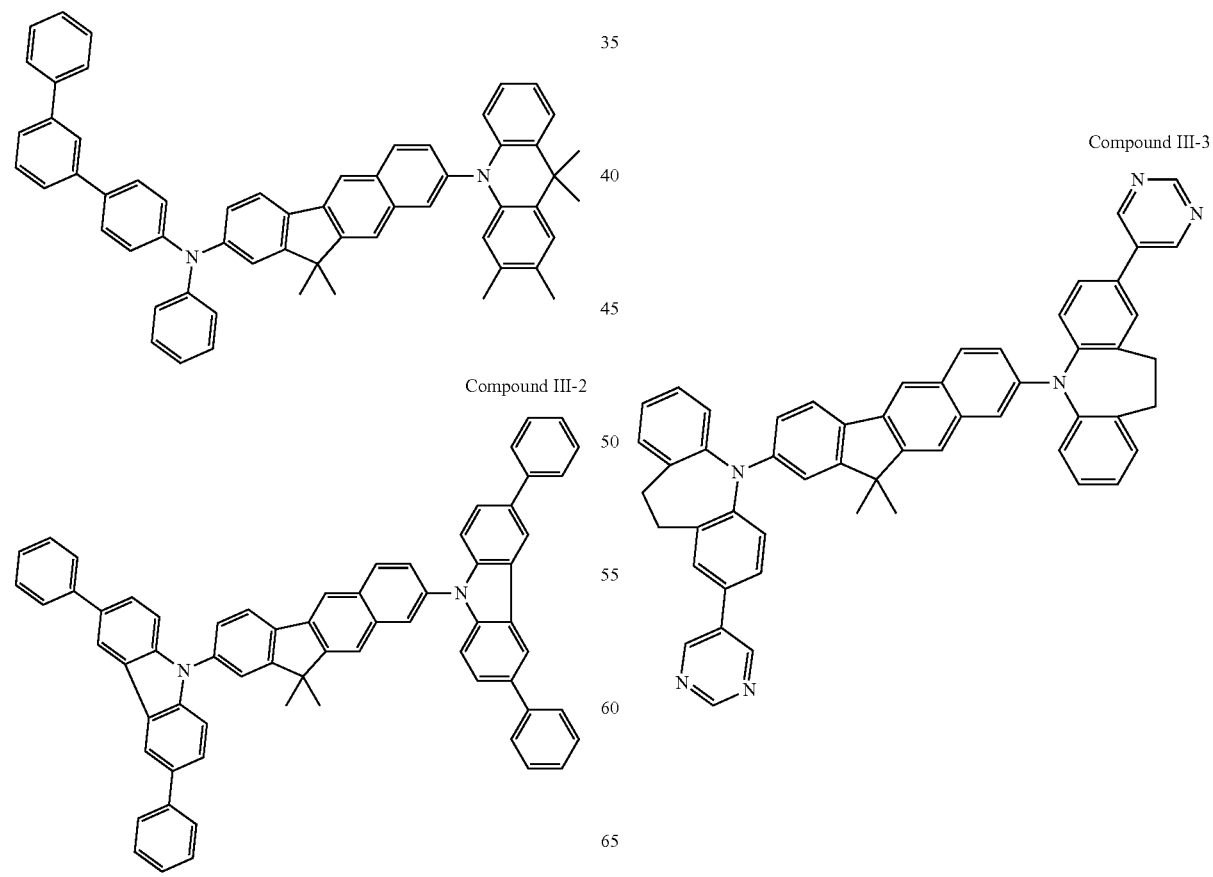

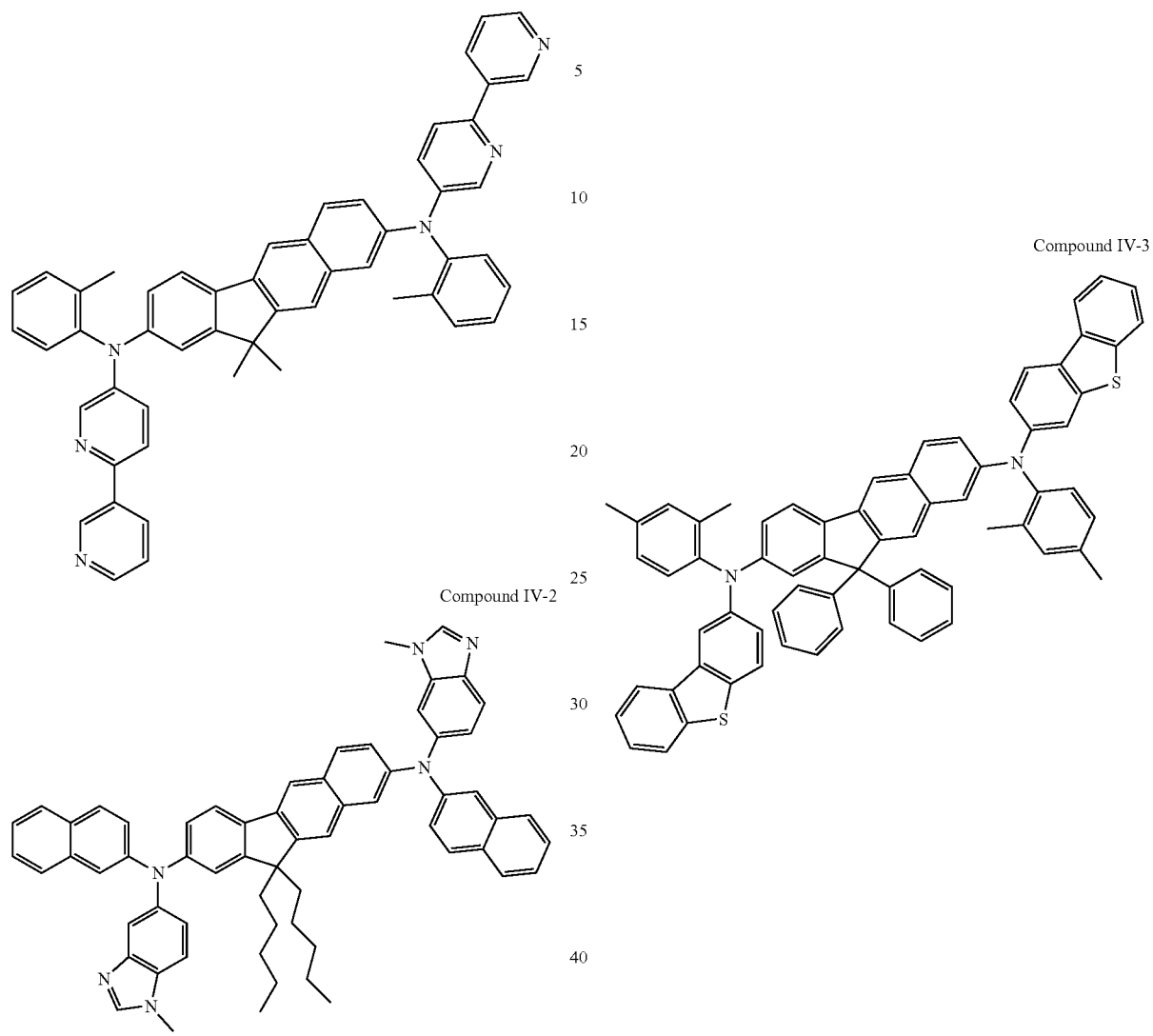
Compound IV-1
Compound IV-2
Compound IV-3
Compound V-1

Compound V-2
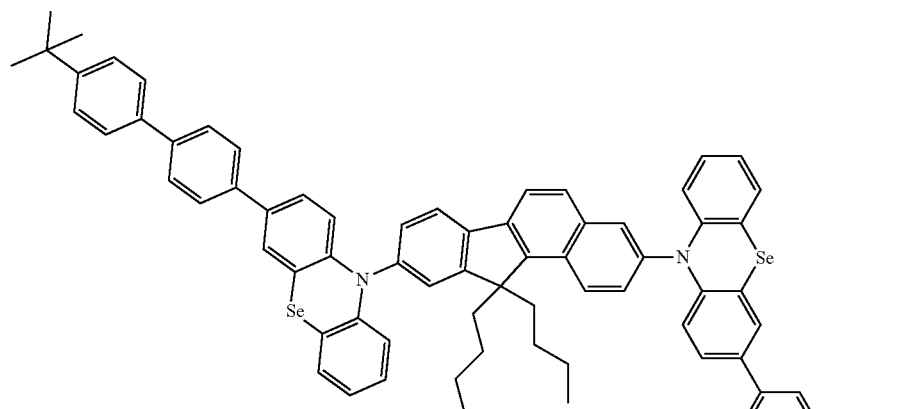
Compound V-3
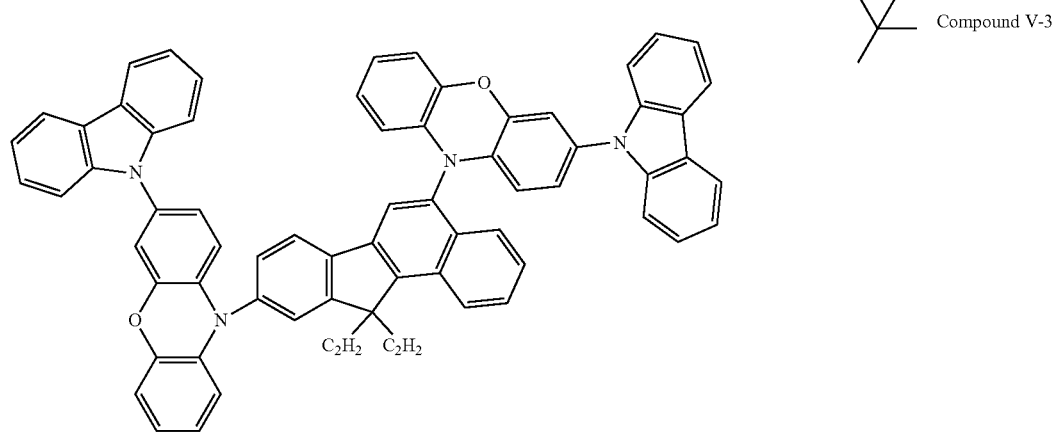
Compound VI-1
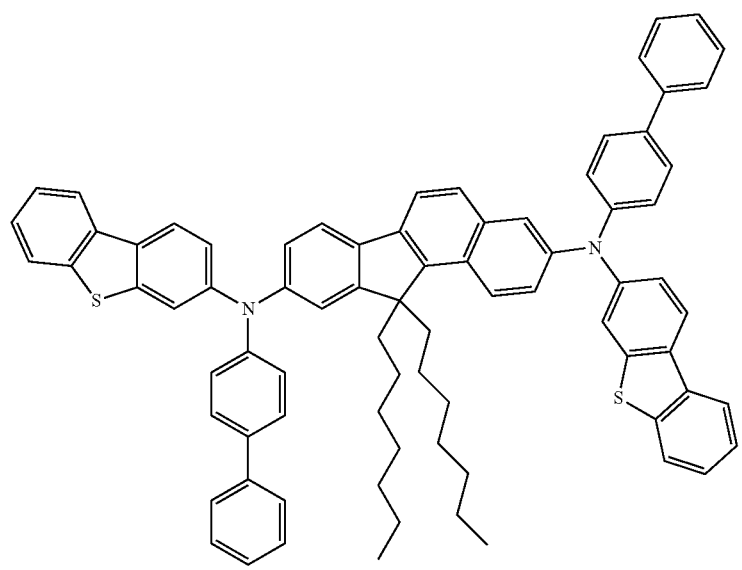

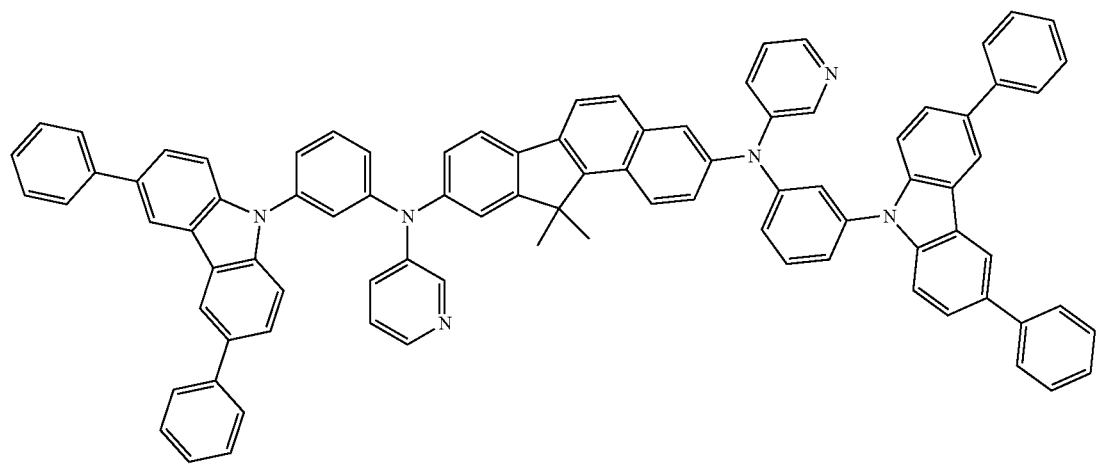
Compound VI-2
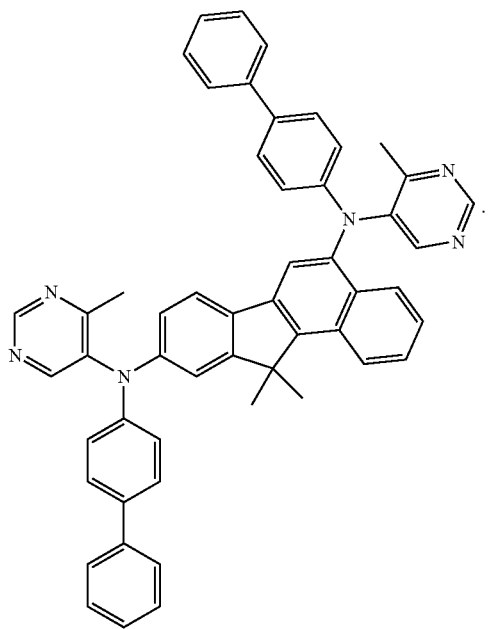
Compound VI-3

15. An electronic device comprising an anode and a cathode with a photoactive layer therebetween, wherein the photoactive layer comprises a compound having Formula I, Formula II, Formula III, Formula IV, Formula V, or Formula VI:

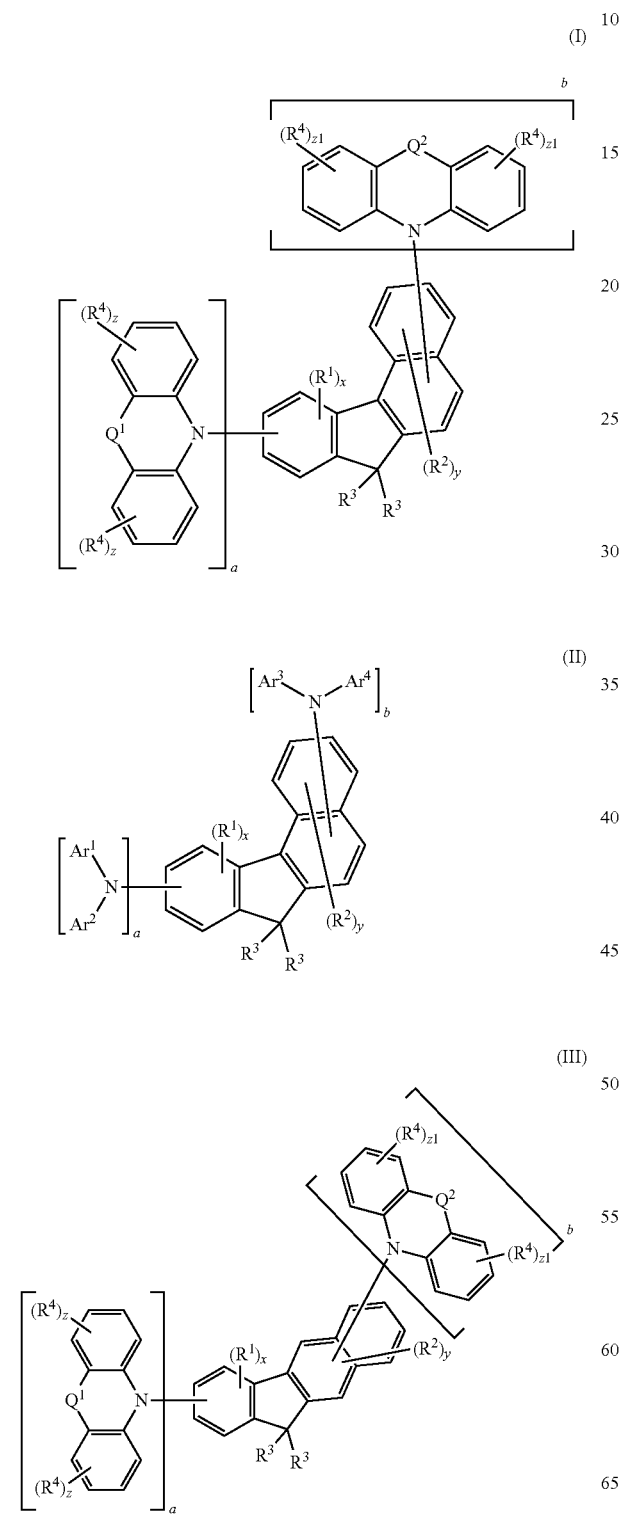

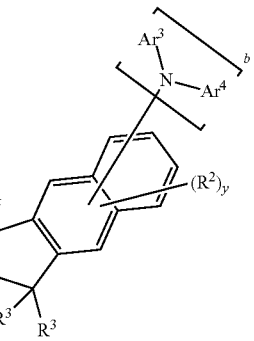

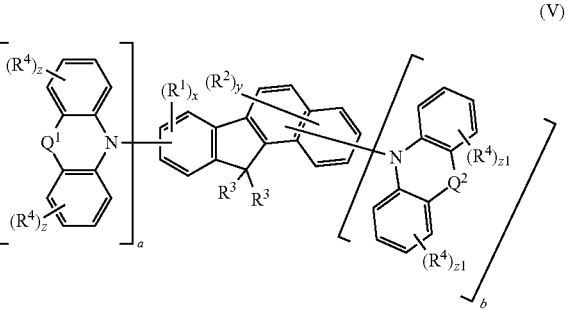

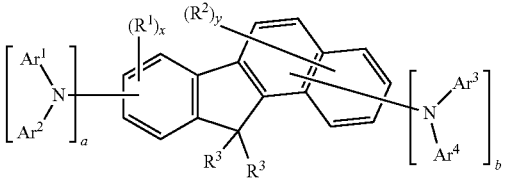

wherein:
Ar¹ and Ar⁴ are the same or different and are heteroaryl or deuterated heteroaryl, Ar² and Ar³ are the same or different and are hydrocarbon aryl, and where Ar¹-Ar⁴ can be substituted with a group selected from the group consisting of D, F, CN, alkyl, fluoroalkyl, aryl, N-heteroaryl, silyl, germyl, deuterated alkyl, deuterated partially-fluorinated alkyl, deuterated aryl, deuterated heteroaryl, deuterated silyl, and deuterated germyl;

Q¹ and Q² are the same or different and are selected from the group consisting of nil, a single bond connecting the two aryl groups on the nitrogen, $(CR^5_2)_w$, $NR^6$, O, S, and Se, with the proviso that at least one of Q¹ and Q² is not nil;

R¹, R² and R⁴ are the same or different at each occurrence and are selected from the group consisting of D, F, CN, alkyl, alkoxy, fluoroalkyl, aryl, aryloxy, heteroaryl, silyl, siloxane, siloxy, germyl, deuterated alkyl, deuterated partially-fluorinated alkyl, deuterated alkoxy, deuterated aryl, deuterated heteroaryl, deuterated heteroaryl deuterated silyl, deuterated siloxane, deuterated siloxy, and deuterated germyl;

R³ is the same or different at each occurrence and is selected from the group consisting of alkyl, silyl, germyl, aryl, and deuterated analogs thereof, where two alkyl R³ groups can be joined together to make a cycloalkyl spiro ring, and where two R³ phenyl groups can be joined to form a spiro fluorene group;

R⁵ is the same or different at each occurrence and is selected from the group consisting of H, D, F, alkyl, fluoroalkyl, deuterated alkyl, or deuterated partially-fluorinated alkyl;

R6 is selected from the group consisting of aryl and deuterated aryl;

a and b are the same or different and are 0 or 1, with the proviso that a+b≥1, and with the proviso that when a=1 and b=0, Q1 is not a single bond, and, in Formula V, with the proviso that when a=1 and b=0, Q1 is not $NR_6$;

w is an integer of 1-6;

x is an integer of 0-4, with the proviso that when a=1, x=0-3;

y is an integer of 0-6, with the proviso that when b=1, y=0-5;

z is an integer of 0-5, with the proviso that when O1 is not nil, z is 0-4; and z1 is an integer of 0-5, with the proviso that when O2 is not nil, z1 is 0-4.

16. The device of claim 15, wherein the photoactive layer further comprises a host material selected from the group consisting of anthracenes, chrysenes, pyrenes, phenanthrenes, triphenylenes, phenanthrolines, naphthalenes, triazines, quinolines, isoquinolines, quinoxalines, phenylpyridines, benzodifurans, metal quinolinate complexes, indolofluorenes, indolocarbazoles, indoloindoles, deuterated analogs thereof, and combinations thereof.

17. The device of claim 15, wherein a=b=1.

18. The device of claim 15, wherein the N-heteroaryl is selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, indole, indoloindole, substituted derivatives thereof, and deuterated analogs thereof.

* * * * *